United States Patent
Sucharov et al.

(10) Patent No.: US 9,512,481 B2
(45) Date of Patent: Dec. 6, 2016

(54) POLYMORPHISMS IN THE PDE3A GENE

(75) Inventors: Carmen Sucharov, Superior, CO (US); Michael Bristow, Englewood, CO (US); Matthew Taylor, Denver, CO (US); Dobromir Slavov, Aurora, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 13/395,311

(22) PCT Filed: Sep. 13, 2010

(86) PCT No.: PCT/US2010/048629
§ 371 (c)(1),
(2), (4) Date: Nov. 5, 2012

(87) PCT Pub. No.: WO2011/032088
PCT Pub. Date: Mar. 17, 2011

(65) Prior Publication Data
US 2013/0203827 A1   Aug. 8, 2013

Related U.S. Application Data

(60) Provisional application No. 61/241,730, filed on Sep. 11, 2009.

(51) Int. Cl.
*C12Q 1/68* (2006.01)
*A61K 31/00* (2006.01)

(52) U.S. Cl.
CPC ............. *C12Q 1/6883* (2013.01); *A61K 31/00* (2013.01); *C12Q 2600/106* (2013.01); *C12Q 2600/156* (2013.01); *C12Q 2600/158* (2013.01)

(58) Field of Classification Search
CPC . A61K 31/00; C12Q 1/6883; C12Q 2600/106; C12Q 2600/156; C12Q 2600/158
See application file for complete search history.

(56) References Cited

U.S. PATENT DOCUMENTS

| | | | |
|---|---|---|---|
| 4,582,788 A | 4/1986 | Erlich | 435/6.12 |
| 4,627,429 A | 12/1986 | Tsuk | 604/307 |
| 4,656,127 A | 4/1987 | Mundy | 435/6.12 |
| 4,659,774 A | 4/1987 | Webb et al. | 525/54.2 |
| 4,682,195 A | 7/1987 | Yilmaz | 257/144 |
| 4,683,194 A | 7/1987 | Saiki et al. | 435/6.12 |
| 4,683,195 A | 7/1987 | Mullis et al. | 435/6.11 |

(Continued)

FOREIGN PATENT DOCUMENTS

| | | |
|---|---|---|
| EP | 50424 | 4/1982 |
| EP | 84796 | 8/1983 |

(Continued)

OTHER PUBLICATIONS

Movesian et al ("Phosphodiesterase inhibition in heart failure." Heart Fail Rev. 2009; 14:255-263).*

(Continued)

*Primary Examiner* — Wu-Cheng Winston Shen
*Assistant Examiner* — Rayna B Rodriguez
(74) *Attorney, Agent, or Firm* — Norton Rose Fulbright US LLP

(57) ABSTRACT

Embodiments of the invention are directed to identifying or treating a patient that would benefit from phosphodiesterase inhibitor therapy.

12 Claims, 8 Drawing Sheets

(56) References Cited

U.S. PATENT DOCUMENTS

| | | |
|---|---|---|
| 4,683,202 A | 7/1987 | Mullis ........................ 435/91.2 |
| 4,784,857 A | 11/1988 | Berry et al. ................ 424/449 |
| 4,800,159 A | 1/1989 | Mullis et al. ............... 435/91.2 |
| 4,816,571 A | 3/1989 | Andrus et al. .............. 536/25.3 |
| 4,883,750 A | 11/1989 | Whiteley et al. ........... 435/6.16 |
| 4,946,773 A | 8/1990 | Maniatis et al. ............ 435/6.11 |
| 4,959,463 A | 9/1990 | Froehler ..................... 536/25.3 |
| 4,965,188 A | 10/1990 | Mullis et al. ............... 435/6.12 |
| 5,126,145 A | 6/1992 | Evenstad et al. ............ 424/465 |
| 5,130,238 A | 7/1992 | Malek et al. ............... 435/91.21 |
| 5,141,813 A | 8/1992 | Nelson ........................ 428/402 |
| 5,169,766 A | 12/1992 | Schuster et al. ............ 435/91.2 |
| 5,210,420 A | 5/1993 | Hartz et al. ............... 250/363.03 |
| 5,264,566 A | 11/1993 | Froehler et al. ........... 536/25.34 |
| 5,279,721 A | 1/1994 | Schmid ........................ 204/457 |
| 5,428,148 A | 6/1995 | Reddy et al. ............... 536/26.8 |
| 5,554,744 A | 9/1996 | Bhongle et al. ............ 536/25.3 |
| 5,574,146 A | 11/1996 | Reddy et al. .............. 536/25.34 |
| 5,602,244 A | 2/1997 | Caruthers et al. .......... 536/25.6 |
| 5,605,798 A | 2/1997 | Koster ............................. 435/5 |
| 5,645,897 A | 7/1997 | Andra ........................... 427/526 |
| 5,662,925 A | 9/1997 | Ebert et al. .................. 424/447 |
| 5,705,629 A | 1/1998 | Bhongle ..................... 536/25.34 |
| 5,788,983 A | 8/1998 | Chien et al. ................. 424/449 |
| 5,840,873 A | 11/1998 | Nelson et al. .............. 536/24.3 |
| 5,843,640 A | 12/1998 | Patterson et al. ................ 435/5 |
| 5,843,650 A | 12/1998 | Segev ............................ 435/6.1 |
| 5,843,651 A | 12/1998 | Stimpson et al. ........... 435/6.11 |
| 5,843,663 A | 12/1998 | Stanley et al. .............. 435/6.11 |
| 5,846,708 A | 12/1998 | Hollis et al. ..................... 506/12 |
| 5,846,709 A | 12/1998 | Segev ............................ 435/6.1 |
| 5,846,717 A | 12/1998 | Brow et al. .................. 435/6.18 |
| 5,846,726 A | 12/1998 | Nadeau et al. .............. 435/6.12 |
| 5,846,729 A | 12/1998 | Wu et al. ..................... 435/6.12 |
| 5,846,783 A | 12/1998 | Wu et al. ..................... 435/91.2 |
| 5,849,481 A | 12/1998 | Urdea et al. ................. 435/6.11 |
| 5,849,483 A | 12/1998 | Shuber ............................... 435/5 |
| 5,849,486 A | 12/1998 | Heller et al. ................. 435/6.11 |
| 5,849,487 A | 12/1998 | Hase et al. ................... 435/6.12 |
| 5,849,497 A | 12/1998 | Steinman ..................... 435/6.11 |
| 5,849,546 A | 12/1998 | Sousa et al. .................. 435/91.5 |
| 5,849,547 A | 12/1998 | Cleuziat et al. ............ 435/91.21 |
| 5,851,770 A | 12/1998 | Babon et al. ................. 435/6.14 |
| 5,851,772 A | 12/1998 | Mirzabekov et al. ....... 435/6.14 |
| 5,853,990 A | 12/1998 | Winger et al. ............... 435/6.18 |
| 5,853,992 A | 12/1998 | Glazer et al. ................. 435/6.12 |
| 5,853,993 A | 12/1998 | Dellinger et al. ........... 435/6.14 |
| 5,856,092 A | 1/1999 | Dale et al. ................... 435/6.11 |
| 5,858,652 A | 1/1999 | Laffler et al. ...................... 435/5 |
| 5,861,244 A | 1/1999 | Wang et al. .................. 435/6.11 |
| 5,863,732 A | 1/1999 | Richards ........................ 435/6.1 |
| 5,863,753 A | 1/1999 | Haugland et al. ............ 435/34 |
| 5,866,331 A | 2/1999 | Singer et al. ................. 435/6.11 |
| 5,866,337 A | 2/1999 | Schon ............................ 435/6.18 |
| 5,866,366 A | 2/1999 | Kallender ..................... 435/69.1 |
| 5,900,481 A | 5/1999 | Lough et al. ..................... 506/30 |
| 5,905,024 A | 5/1999 | Mirzabekov et al. ........ 435/6.12 |
| 5,910,407 A | 6/1999 | Vogelstein et al. .......... 435/6.14 |
| 5,912,124 A | 6/1999 | Kumar .......................... 435/6.12 |
| 5,912,145 A | 6/1999 | Stanley ......................... 435/91.1 |
| 5,912,148 A | 6/1999 | Eggerding .................... 435/91.2 |
| 5,916,776 A | 6/1999 | Kumar .......................... 435/91.1 |
| 5,916,779 A | 6/1999 | Pearson et al. ............... 435/91.2 |
| 5,919,626 A | 7/1999 | Shi et al. ...................... 435/6.14 |
| 5,919,630 A | 7/1999 | Nadeau et al. ............... 435/6.12 |
| 5,922,574 A | 7/1999 | Minter .......................... 435/91.1 |
| 5,924,417 A | 7/1999 | Braithwaite ............. 128/203.15 |
| 5,925,525 A | 7/1999 | Fodor et al. ....................... 506/3 |
| 5,928,862 A | 7/1999 | Morrison ..................... 435/6.18 |
| 5,928,869 A | 7/1999 | Nadeau et al. ............... 435/6.18 |
| 5,928,870 A | 7/1999 | Lapidus et al. .............. 435/6.14 |
| 5,928,905 A | 7/1999 | Stemmer et al. ............. 435/91.1 |
| 5,928,906 A | 7/1999 | Koster et al. ................. 435/91.2 |
| 5,929,227 A | 7/1999 | Glazer et al. ................. 536/26.6 |
| 5,932,413 A | 8/1999 | Celebuski .................... 435/6.11 |
| 5,932,451 A | 8/1999 | Wang et al. .................. 435/91.21 |
| 5,935,791 A | 8/1999 | Nadeau et al. ............... 435/6.18 |
| 5,935,825 A | 8/1999 | Nishimura et al. ........... 435/91.2 |
| 5,939,291 A | 8/1999 | Loewy et al. ................ 435/91.2 |
| 5,942,391 A | 8/1999 | Zhang et al. ................. 435/6.12 |
| 5,952,174 A | 9/1999 | Nikiforov et al. ........... 435/6.11 |
| 5,998,458 A | 12/1999 | Bristow ........................ 514/392 |
| 6,113,940 A | 9/2000 | Brooke et al. ............... 424/449 |
| 6,203,776 B1 | 3/2001 | Bristow et al. ................ 424/9.2 |
| 6,706,686 B2 | 3/2004 | Long et al. ................... 424/94.4 |
| 6,946,441 B2 | 9/2005 | Long et al. ................... 514/15.6 |
| 7,049,066 B2 | 5/2006 | Bristow et al. .............. 435/6.12 |
| 7,482,331 B1 | 1/2009 | Bristow et al. .............. 514/44 R |
| 7,678,824 B2 | 3/2010 | Liggett et al. ................ 514/415 |
| 8,080,578 B2 | 12/2011 | Liggett et al. ................ 514/415 |
| 8,093,286 B2 | 1/2012 | Liggett et al. ................ 514/415 |
| 2004/0265849 A1 | 12/2004 | Cargill et al. ..................... 435/6 |
| 2008/0145359 A1 | 6/2008 | Bicknell et al. ............ 424/130.1 |
| 2008/0227844 A1 | 9/2008 | Liggett et al. ................ 514/415 |

FOREIGN PATENT DOCUMENTS

| | | |
|---|---|---|
| EP | 201184 | 12/1986 |
| EP | 237362 | 9/1987 |
| EP | 258017 | 3/1988 |
| EP | 266032 | 5/1988 |
| EP | 320308 | 6/1989 |
| EP | 329822 | 8/1989 |
| FR | 2650840 | 2/1991 |
| GB | 2202328 | 9/1988 |
| WO | PCT/US87/00880 | 10/1987 |
| WO | WO 88/10315 | 12/1988 |
| WO | WO 89/06700 | 7/1989 |
| WO | PCT/US89/01025 | 10/1989 |
| WO | WO 90/01069 | 2/1990 |
| WO | WO 91/02087 | 2/1991 |
| WO | WO 92/15712 | 9/1992 |
| WO | WO 93/22456 | 11/1993 |
| WO | WO 95/11995 | 5/1995 |
| WO | WO 2004/017377 | 8/2004 |
| WO | WO 2005/058280 A2 * | 6/2005 |
| WO | WO 2009/012468 A2 * | 1/2009 |

OTHER PUBLICATIONS

Prickett et al ("Gene therapy in cystic fibrosis." "Gene Therapy in cystic fibrosis." Translational research: the journal of laboratory and clinical medicin. Apr. 2013;161(4):255-64. doi: 10.1016/j.trsl.2012.12.001. Epub Dec. 26, 2012).*
U.S. Appl. No. 09/415,733, filed Oct. 12, 1999, Bristow.
U.S. Appl. No. 10/241,368, filed Sep. 11, 2002, Bristow.
U.S. Appl. No. 11/010,830, filed Dec. 13, 2004, Bristow.
U.S. Appl. No. 11/067,502, filed Feb. 25, 2005, Bristow.
U.S. Appl. No. 11/087,059, filed Mar. 22, 2005, Bristow.
U.S. Appl. No. 11/087,076, filed Mar. 22, 2005, Bristow.
U.S. Appl. No. 11/138,894, filed May 26, 2005, Gerber.
U.S. Appl. No. 11/190,074, filed Jul. 26, 2005, Long.
U.S. Appl. No. 11/215,844, filed Aug. 30, 2005, Long.
U.S. Appl. No. 13/056,916, filed May 4, 2011, Bristow.
U.S. Appl. No. 13/309,114, filed Dec. 1, 2011, Liggett.
U.S. Appl. No. 13/518,471, Bristow.
Barany, et al., *Proc. Natl. Acad. Sci.* USA, 88:189-193, 1991.
Bartholomew et al, *Oncogene*, 9:939-942, 1994.
Copeland et al., *Adv Cancer Res.*, 54:141-57, 1990.
De Arruda et al., *Expert. Rev. Mol. Diagn.* 2:487-496, 2002.
Delwel et al *Mol Cell Biol*, 13(7):4291-300, 1993.
Di Polo, et al., *Invest Opthalmol Vis Sci*, 37:551-560, 1996.
Ding et al., *Circulation* 11:2469-2476, 2005.
Durand et al., *Ann. Med.*, 27:311-317, 1995.
Froehler et al., *Nucleic Acids Res.*, 14(13):5399-5407, 1986.
Frohman, In: PCR Protocols: A Guide to Methods and Applications, Academic Press, N.Y., 1990.
Funabiki et al *Oncogene*, 9(6):1575-81, 1994.
Goyama et al. *Cell Stem Cell*, 3(2):207-20, 2008.
Halushka et al., *Nat. Genet.*, 22(3):239-247, 1999.

(56) References Cited

OTHER PUBLICATIONS

Hirai, H., *Int J Biochem Cell Biol*, 31(12):1367-71, 1999.
Humphries, et al., In: *Molecular Diagnosis of Genetic Diseases*, Elles (Ed.), 321-340, 1996.
Inazuka et al., *Genome Res*, 7(11):1094-1103, 1997.
Innis et al., *Proc. Natl. Acad. Sci.* USA 85(24):9436-9440, 1988.
Izutsu et al *Blood* 97(9):2815-22, 2001.
Johnson et al., *Nat. Genet.*, 29(2):233-237, 2001.
Jolkowska et al *Leuk Res* 24(7):553-8, 2000.
Jones, *Nature*, 199:280-282, 1963.
Ke and Cardon *Bioinformatics*, 19(2):297-288, 2003.
Kim et al *Oncogene*, 17(12):1527-38, 1998.
Klaassen's The Pharmacological Basis of Therapeutics.
Komher, et al., *Nucl. Acids. Res.* 17:7779-7784, 1989.
Kuppuswamy et al., *Proc. Natl. Acad. Sci. USA*, 88:1143-1147, 1991.
Kurokawa et al *Nature*, 394(6688):92-6, 1998.
Kurokawa et al *EMBO J*, 19(12):2958-68, 2000.
Kwoh et al., *Proc. Natl. Acad. Sci. USA*, 86:1173-1177, 1989.
Kwok and Chen, *Curr Issues Mol. Biol.*, 5(2):43-60, 2003.
Kwok et al., *Genomics*, 23(1):138-144, 1994.
Kwok et al., *Genomics*, 31(1):123-6, 1996.
Kwok, *Annu. Rev. Genomics Hum. Genet.*, 2:235-258, 2001.
Landegren et al., *Science* 241:1077-1080, 1988.
Lu et al., *Biopolymers*, 73:606-613, 2004.
Maisel et al *Annals of Internal Medicine*, 110:195-201, 1989.
Matsugi et al., *Mol Cell Biol*, 10(3):1259-64, 1990.
Maxam et al., *Proc. Natl. Acad. Sci. USA*, 74:560, 1977.
Metra et al., *European Heart Journal*, doi:10.1093/eurheartj/ehp338, 2009.
Meyers et al., *Science*, 230:1342, 1985.
Modrich, *Ann. Rev. Genet.*, 25:229-253, 1991.
Morishita, et al., *Cell*, 54(6):831-40, 1988.
Morishita, et al., *Oncogene*, 5(9):1419-23, 1990.
Morishita et al., *Oncogene Res*, 5(3):221-31, 1990.
Movsesian, *J. Am. Coll. Cardiol.*, 34:318-324, 1999.

Mullis et al., *Cold Spring Harbor Symp. Quant. Biol.* 51:263-273, 1986.
Nickerson et al., *Proc. Natl. Acad. Sci. USA*, 87:8923-8927, 1990.
Nyren et al., *Anal. Biochem.* 208:171-175, 1993.
Ohara et al., *Proc. Natl. Acad. Sci. USA*, 86:5673-5677, 1989.
Orita et al., *Genomics*, 5:874-879, 1989.
Palmer et al *J Biol Chem* 276(28):25834-40, 2001.
Patent Cooperation Treaty International Search Report in PCT/US2010/048629 issued Nov. 24, 2010.
Perkins et al *Development*, 111(2):479-87, 1991.
Prezant et al., *Hum. Mutat.*, 1:159-164, 1992.
Qui et al *Biochemistry*, 47(12):3697-704, 2008.
Random Primer 24, Datasheet, New England Biolabs, 2004 http://web.archive.org/web/20040618195247/ http://www.neb.com/nebecomm/products/products1256.asp.
Reinhardt et al., *J. Clin. Invest.*, 95:1528-1539, 1995.
Remington's Pharmaceutical Sciences, 15$^{th}$ Edition, pp. 1035-1038 and 1570-1580, 1990.
Ruano et al., *Nucl. Acids Res.*, 19:6877-6882, 1991.
Ruano et al., *Nucl. Acids Res.*, 17:8392, 1989.
Sanger et al., *J. Molec. Biol.*, 94:441, 1975.
Shakur et al., *Prog. Nucleic Acids Res. Mol. Biol.*, 66:241-277, 2000.
Sheffield et al., *Proc. Natl. Acad Sci. USA*, 86:232-236, 1989.
Small et al., *Methods Enzymol*, 343:459-75, 2002.
Sokolov, *Nucl. Acids Res.* 18:3671, 1990.
Stevens et al., *Biotechniques*, 34:198-203, 2003.
Syvanen et al., *Genomics* 8:684-692, 1990.
Taillon-Miller et al., *Genome Res*, 8(7):748-754, 1998.
Turki et al., *J. Clin. Invest.*, 95:1635-1641, 1996.
Ugozzoll et al., *GATA* 9:107-112, 1992.
Walker et al., *Proc. Natl. Acad. Sci. USA*, 89:392-396, 1992.
Wang and Dhalla, *Mol. Cell Biochem*, 214:131-155, 2000.
Wartell et al., *Nucl. Acids Res.*, 18:2699-2706, 1990.
Winter et al., *Proc. Natl. Acad. Sci. USA*, 82:7575, 1985.
Movsesian, et al., *J Clin Invest.* 88:15-19, 1991.
Movsesian, et al., *Heart Fail Rev.* 14:255-63, 2009.
Bristow, *Circ Res.* 109:1176-94, 2011.

\* cited by examiner

SEQUENCE LISTING

<160> NUMBER OF SEQ ID NOS: 7

<210> SEQ ID NO 1
<211> LENGTH: 15
<212> TYPE: DNA
<213> ORGANISM: Artificial Sequence
<220> FEATURE:
<223> OTHER INFORMATION: Synthetic primer

<400> SEQUENCE: 1

```
tatctactta tgtca                                              15
```

<210> SEQ ID NO 2
<211> LENGTH: 29
<212> TYPE: DNA
<213> ORGANISM: Artificial Sequence
<220> FEATURE:
<223> OTHER INFORMATION: Synthetic primer

<400> SEQUENCE: 2

```
ttctcatatc tacttatgtc ataatatta                               29
```

<210> SEQ ID NO 3
<211> LENGTH: 1874
<212> TYPE: DNA
<213> ORGANISM: Artificial Sequence
<220> FEATURE:
<223> OTHER INFORMATION: Synthetic primer

<400> SEQUENCE: 3

```
gccaacagat atgaatgatt tccaatcaa ggttttttcac tccgatgtgt cccaggtagg    60
atctggcata tgaatcatat gtctaaaaag gaaactcatg aaagtatgtg tgcgtgctag   120
ggggctcatt tgtctttggc aaagacattg ctgctcctgt ttccttaatt attaaacaga   180
tggtgcccac tgccattgac tagctgccca actcatactc ctgtgtggta gcacaattct   240
ggacatctga cagagagaag ctataccttt atagtttctc atatctactt atgtcataat   300
attaatatct gccttctact agaacaggct gcttcccatg aagctgttta aacttaagt    360
catcttctcc ccctgtcccc ataaattaat tttatctcaa ggatctcctt ttggcttttt   420
ttattgcttc atgtctacat acaaaataca gtggcatatt gaatcaatta tctaaatgct   480
ctaggctgta aatacacttt aacctggaat gtcaagataa ttaagacaaa attggattat   540
taagattatt attagtgagg gcaaatgaca tctaagatag ccatgttaaa agtggagtat   600
catattaaaa agacaactag atcccaggga acatcaatag agtttaagtc cattgaacag   660
atactgaatt cttttttcata atctgccaaa aaaaggttag cttgaaaatt ttcttttagt   720
ttctcaaata tcacactgct gcagtacacg aacctttact cattaataac taaggtcctg   780
atttttttca tatgctttgc tcgaagatgt agtattttgc agccatagac agtcttctaa   840
gayctctcct agtgttaacc cacctatcct cacctctccc ttgagatttt tctttatttt   900
ttgatgaact atctgggctt ttaaactttg ttaaccttt tgaggatac ggtcacttaa     960
tctcaatgta attttacttt ccacagtcaa aaactattgt gtaatactca tgcactggat  1020
ttaaatgact gctgcctctc cttcctttct ttttatacta ttgtggtcta ggtaaggctg  1080
attcttccat catttgaacc aacaggccag gcttgggttc tcataaagca gaccttccag  1140
caggagcgac caaaggatga cactgtcacc tgaaattgga ctgctgttgt acctgacttg  1200
ggaacatctt tgaatcagac agtagaagtg gctgtcattt tcagggacag tagaaagtat  1260
gttggctctc atctgccaag taggcaaaca caatcttttt ttttttttttt tccttccaac  1320
gttctaggga gctcagcctc agggctagcc gcagcccccc acaccccggg gctgcggtgg  1380
gctgcgcggt ggatcagcct cagcagcccc tgctccagcc tgtagggtga accggccgct  1440
ttcccagcaa aggagcaatc gagctgaggg tagcgcctcc tccgcaggag ggggcgggag  1500
ctcggctgag aaagctttcc tagggagttg ccttaaagaa agaaagcgga attgtcgatc  1560
actccagttg ccagttttat acaatttaa gcagtcgtcg ccactcgttt cccctttgca  1620
```

|   |   |
|---|---|
| aaactgcaaa tcaccaccaa ccttgcatca aatagaagtg gggagggaaa aaaaaagcaa | 1680 |
| atctccttct cccttctcac cctcccttc ttctcaccct cccttcctct cttactcgct | 1740 |
| ccttctccct ccctcccttc tgcggctgcc gctagtctct cggtctggct ctctctccga | 1800 |
| cgggacttag caacttctta tttctcagcc ccttgtccat ttttttttt ccatcctttg | 1860 |
| ccatgaattg gatt | 1874 |

<210> SEQ ID NO 4
<211> LENGTH: 1845
<212> TYPE: DNA
<213> ORGANISM: Artificial Sequence
<220> FEATURE:
<223> OTHER INFORMATION: Synthetic primer

<400> SEQUENCE: 4

|   |   |
|---|---|
| gccaacagat atgaatgatt ttccaatcaa ggttttcac tccgatgtgt cccaggtagg | 60 |
| atctggcata tgaatcatat gtctaaaaag gaaactcatg aaagtatgtg tgcgtgctag | 120 |
| ggggctcatt tgtctttggc aaagacattg ctgctcctgt ttccttaatt attaaacaga | 180 |
| tggtgcccac tgccattgac tagctgccca actcatactc ctgtgtggta gcacaattct | 240 |
| ggacatctga cagagagaag ctataccttt atagtatatc tgccttctac tagaacaggc | 300 |
| tgcttcccat gaagctgttt aaaacttaag tcatcttctc ccctgtccc cataaattaa | 360 |
| ttttatctca aggatctcct tttggctttt tttattgctt catgtctaca tacaaaaatac | 420 |
| agtggcatat tgaatcaatt atctaaatgc tctaggctgt aaatacactt taacctggaa | 480 |
| tgtcaagata attaagacaa aattggatta ttaagattat tattagtgag ggcaaatgac | 540 |
| atctaagata gccatgttaa aagtggagta tcatattaaa aagacaacta gatcccaggg | 600 |
| aacatcaata gagtttaagt ccattgaaca gatactgaat tcttttttcat aatctgccaa | 660 |
| aaaaaggtta gcttgaaaat tttcttttag tttctcaaat atcacactgc tgcagtacac | 720 |
| gaaccttac tcattaataa ctaaggtcct gatttttttc atatgctttg ctcgaagatg | 780 |
| tagtatttg cagccataga cagtcttcta agayctctcc tagtgttaac ccacctatcc | 840 |
| tcacctctcc cttgagattt ttctttattt tttgatgaac tatctgggct tttaaacttt | 900 |
| gttaaccttt tttgaggata cggtcactta atctcaatgt aattttactt tccacagtca | 960 |
| aaaactattg tgtaatactc atgcactgga tttaaatgac tgctgcctct ccttcctttc | 1020 |
| tttttatact attgtggtct aggtaaggct gattcttcca tcatttgaac caacaggcca | 1080 |
| ggcttgggtt ctcataaagc agaccttcca gcaggagcga ccaaaggatg acactgtcac | 1140 |
| ctgaaattgg actgctgttg tacctgactt gggaacatct ttgaatcaga cagtagaagt | 1200 |
| ggctgtcatt ttcagggaca gtagaaagta tgttggctct catctgccaa gtaggcaaac | 1260 |
| acaatctttt tttttttttt ttccttccaa cgttctaggg agctcagcct cagggctagc | 1320 |
| cgcagccccc cacaccccgg ggctgcggt ggctgcgcgg tggatcagcc tcagcagccc | 1380 |
| ctgctccagc ctgtagggtg aaccggccgc tttcccagca aaggagcaat cgagctgagg | 1440 |
| gtagcgcctc ctccgcagga gggggcggga gctcggctga aaagctttc ctagggagtt | 1500 |
| gccttaaaga aagaaagcgg aattgtcgat cactccagtt gccagttta tacaattta | 1560 |
| agcagtcgtc gccactcgtt tccccttgc aaaactgcaa atcaccacca ccttgcatc | 1620 |
| aaatagaagt ggggagggaa aaaaaagca atctccttc tcccttctca ccctcccttt | 1680 |
| cttctcaccc tccctttcctc tcttactcgc tccttctccc tccctcccttt ctgcggctgc | 1740 |
| cgctagtctc tcggtctggc tctctctccg acgggactta gcaacttctt atttctcagc | 1800 |

```
cccttgtcca ttttttttt tccatcctt gccatgaatt ggatt                    1845

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

Asp Gly Ala Thr Ala Asp Gly Ala Asp Trp Ala Gly Ala Thr Ala
1               5                   10                  15

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
ccactgccat tgactagctg                                              20

<210> SEQ ID NO 7
<211> LENGTH: 22
<212> TYPE: DNA
<213> ORGANISM: Artificial Sequence
<220> FEATURE:
<223> OTHER INFORMATION: Synthetic primer

<400> SEQUENCE: 7
gccaaaagga gatccttgag at                                           22
```

POLYMORPHISMS IN THE PDE3A GENE

This application is a national phase application under 35 U.S.C. §371 of International Application No. PCT/US2010/048629 filed Sep. 13, 2010 which claims benefit of priority to U.S. Provisional Application Ser. No. 61/241,730, filed Sep. 11, 2009, the entire contents of which are hereby incorporated by reference.

BACKGROUND OF THE INVENTION

I. Field of the Invention

Embodiments of this invention are directed generally to biology, molecular genetics, and medicine. Certain embodiments are directed to identifying a patient that would benefit from phosphodiesterase inhibitor therapy.

II. Background

Cardiac hypertrophy in response to an increased workload imposed on the heart is a fundamental adaptive mechanism. It is a specialized process reflecting a quantitative increase in cell size and mass (rather than cell number) as the result of any, or a combination of, neural, endocrine or mechanical stimuli. When heart failure occurs, the left ventricle usually is hypertrophied and dilated and indices of systolic function, such as ejection fraction, are reduced. Clearly, the cardiac hypertrophic response is a complex syndrome and the elucidation of the pathways leading to cardiac hypertrophy and systolic dysfunction will be beneficial in the treatment of heart disease resulting from various stimuli. There remains a need for additional treatments for patients suffering from heart failure.

SUMMARY OF THE INVENTION

Chronic activation of the β-Adrenergic Receptor (β-AR) can have deleterious effects on the heart, and animal models over-expressing the β-AR develop heart failure. In the classical β-AR pathway, activation of the receptor results in increased cyclic AMP (cAMP) levels. However, β-ARs are desensitized in the failing heart and cAMP levels are decreased. Phosphodiesterase 3A (PDE3A) hydrolyzes cAMP in certain subcelluar compartments in cardiac myocytes, regulating cAMP levels and subsequent protein kinase A mediated cell signaling. Since cAMP is reduced in certain important cardiac myocyte subcellular compartments such as the microdomain occupied by phospholamban and SR Ca2+ ATPase, it has been postulated that PDE3A inhibition will benefit the heart failure clinical syndrome by restoring cAMP levels in the phospholamban microdomain/suncellular compartment. However, a recently published large clinical trial showed benefits of a PDE3 inhibitor on only a subset of patients. Here we show that the promoter region of PDE3A contains a 29 nucleotide insertional polymorphism (SEQ ID NO:2) that renders the PDE3A promoter non-responsive to increased cAMP levels. The inventors demonstrate that increased cAMP levels in the cardiac cell, mediated by isoproterenol, a cAMP analogue or PDE3A inhibition, results in increased promoter activity when the promoter construct lacks the 29 nucleotide sequence. However, promoter activity does not go up when the sequence is present. Similarly, mRNA levels for heart failure patients containing the insertion polymorphism were not up-regulated in response to PDE3A inhibition treatment while mRNA levels for patients lacking this region were up-regulated 2-fold in response to treatment. These results indicate that only patients who are homozygous for the insertion should be treated with a PDE3A inhibition. Inhibition of PDE3A in other patients will create a positive feedback loop that will result in increased PDE3A levels and reduced response to treatment, commonly known as pharmacological tolerance.

Certain embodiments are directed to methods for treating a patient with heart failure comprising treating the patient with an effective amount of a PDE3A inhibitor after the patient is determined to be homozygous for an insertional polymorphism comprising an Evi-1 binding site in the promoter of the phosphodiesterase type 3A (PDE3A) gene. The Evi-1 insertion polymorphism refers to a nucleic acid sequence inserted in the promoter of PDE3A comprising a nucleic acid sequence that is 85, 90, 95, 98, to 100% identical to the nucleic acid sequence of SEQ ID NO:2. In certain aspects the insertional polymorphism comprises an ectotropic viral integration site-1 protein (Evi-1) binding site. In a further aspects the Evi-1 binding site comprises a 5, 10, 15 to 10, 15, 25, 29 nucleotides or more, including all values and ranges there between of the nucleotide sequence of SEQ ID NO:2.

In certain aspects a PDE3A inhibitor is aminone, cilostazol, milrinone, quazinone, siguazodan, trequinsin, or enoximone. In a further aspect the PDE3A inhibitor is enoximone. The PDE3A inhibitor can be administered at a dose of 1, 5, 10, 15, 20, 25, 30, 35, 40, 45, 50 mg to 40, 50, 60, 70, 80, 90, 100, or 150 mg, including all values and ranges there between. In certain aspects the PDE3A inhibitor is administered 1, 2, 3, 4, 5 or more times a day, a week, or a month, including all values and ranges there between.

Certain embodiments are directed to methods for evaluating a heart failure patient comprising analyzing a biological sample from the patient for the presence of an ectotropic viral integration site-1 protein (Evi-1) binding site deletion or insertional polymorphism in the promoter of one or more phosphodiesterase type 3A (PDE3A) genes of the patient, wherein a patient determined to be homozygous for the insertional polymorphism is responsive to PDE3A inhibitor therapy.

In certain aspects the methods described herein can further comprise obtaining a biological sample from the patient. A biological sample can be a blood sample, a buccal smear, a tissue sample, or a primary culture of somatic cells from the patient. In certain aspects analyzing the sample comprises performing nucleic acid sequencing, restriction digestion, allele-specific nucleic acid amplification, single-stranded conformational polymorphism analysis, or allele specific hybridization analysis. The methods described herein can further comprising preparing a report containing information regarding the genotype of one or more PDE3A genes of the patient. In a further aspect the patient has symptoms of or has been diagnosed with heart failure. In still a further aspect the patient is determined to be homozygous for the insertional polymorphism in the PDE3A gene and is subsequently treated with a PDE3A inhibitor.

In certain embodiments the patient is determined not to be homozygous for the insertional polymorphism in the PDE3A gene and is subsequently treated with a non-PDE3A inhibitor treatment.

Further embodiments are directed to methods for evaluating a patient having or at risk of developing heart failure for responsiveness to phosphodiesterase inhibitor therapy comprising obtaining a determination of the patient's genotype for an insertional polymorphism in a phosphodiesterase type 3A (PDE3A) gene, wherein homozygosity for the insertional polymorphism is predictive of responsiveness to phosphodiesterase inhibitor therapy for treating heart failure in the patient. In certain aspects the nucleic acid sequence insertion comprises an ectotropic viral integration site-1 protein (Evi-1) binding site. In a further aspect the Evi-1 binding site has a nucleic acid sequence that is 85, 90, 95, 98, or 100% identical to the nucleic acid sequence of SEQ ID NO:2. The methods can include obtaining a patient history. In certain aspects this includes determination of the patient's genotype for an insertional polymorphism in a phosphodiesterase type 3A (PDE3A) gene by nucleic acid sequencing, restriction digestion, allele-specific nucleic acid amplification, single-stranded conformational polymorphism analysis, or allele specific hybridization analysis. The patient can have symptoms of or has been diagnosed with heart failure. In certain aspects the methods further comprise treating a patient determined to be homozygous for the insertional polymorphism in the PDE3A gene with a PDE3A inhibitor, including but not limited to, enoximone.

Embodiments are directed to methods of determining the efficacy of phosphodiesterase type 3A (PDE3A) inhibition therapy (including but not limited to enoximone) comprising detecting a nucleic acid insertion having a nucleotide sequence that is 80, 85, 90, 95, 98, or 100% identical to the nucleic acid sequence of SEQ ID NO:2 in a promoter of one or both phosphodiesterase type 3A (PDE3A) genes of a subject. The nucleic acid insertion can be within the 2000 nucleotides 5' of the transcription start site. In certain aspects detection of the nucleic acid insertion uses at least one oligonucleotide that anneals to SEQ ID NO:3, SEQ ID NO:4, or SEQ ID NO:3 and SEQ ID NO:4. The detection method can comprise at least one allele specific amplification primer or allele specific nucleic acid probe. The allele specific amplification primer or allele specific nucleic acid probe can specifically hybridizes with an Evi-1 insertion under high stringency conditions. In certain aspects, the probe or primer is labeled with a detectable label. In a further aspect the primer or probe is detectable after hybridization with a PDE3A nucleic acid comprising an Evi-1 insertion. The nucleic acid insertion can be detected using nucleic acid amplification, nucleic acid hybridization, restriction fragment length polymorphism (RFLP) analysis, single stranded conformational polymorphism (SSCP) analysis, nucleic acid sequencing, denaturing high performance liquid chromatography, comparative genome hybridization, and/or Southern blotting. In certain aspects nucleic acid amplification comprises polymerase chain reaction amplification or ligase chain reaction amplification. In a further aspect nucleic acid hybridization detection method comprises an allele specific oligonucleotide probe or a microarray of nucleic acid probes.

Certain embodiments are directed to an isolated nucleic acid sequence comprising nucleotides 269 to nucleotide 307 of SEQ ID NO:3 or a nucleic acid having 85, 90, 95, 98, or 100% identity to SEQ ID NO:2, including all values and ranges there between. In certain aspects the nucleic acid sequence comprises 20, 30, 40, 50, 60, 70, 80, 90, 100, 500, 1000 or more consecutive nucleotides of SEQ ID NO:3 or SEQ ID NO:4, including all values and ranges there between.

A further embodiment is directed to an amplification primer pair comprising two oligonucleotides that amplify a nucleic acid segment comprising nucleotides 274 to 302 of SEQ ID NO:3 or a nucleic acid that is 85, 90, 95, 98, or 100% identical to SEQ ID NO:2. A first primer can comprise the nucleic acid sequence of SEQ ID NO:6 (CCACTGC-CATTGACTAGCTG). A second primer can comprise the nucleic acid sequence of SEQ ID NO:7 (GCCAAAAGGA-GATCCTTGAGAT).

Certain embodiments are directed to a nucleic acid probe that specifically hybridizes to a phosphodiesterase type 3A nucleic acid comprising nucleotides 274 to 302 of SEQ ID NO:3 or a nucleic acid that is 85, 90, 95, 98, or 1005 identical to SEQ ID NO:2. In certain aspects the nucleic acid probe is labeled. In a further aspect the nucleic acid probe is detectable upon binding or hybridization to a PDE3A nucleic acid comprising an Evi-1 insertion.

Another aspect is a kit for genotyping a phosphodiesterase type 3A gene comprising oligonucleotides of at least 10 contiguous nucleotides of SEQ ID NO:3 that amplify a nucleic acid segment comprising an Evi-1 binding site insertional polymorphism or a nucleic acid probe that specifically hybridizes to a PDE3A gene comprising an Evi-1 binding site insertional polymorphism.

To achieve these methods, a doctor, medical practitioner, or their staff may obtain directly from the patient a biological sample for evaluation. The sample may be analyzed by the practitioner or their staff, or it may be sent to an outside or independent laboratory. The medical practitioner may be cognizant of whether the test is providing information regarding the patient's PDE3A genes, or the medical practitioner may be aware only that the test indicates directly or indirectly that the genotype of the patient reflects the insertional polymorphism phenotype ("homozygous for insertional polymorphism" sequence).

Similarly, the medical practitioner may be cognizant of whether the test is providing information regarding the patient's PDE3A genes or the medical practitioner may be aware only that the test indicates directly or indirectly that the genotype of the patient reflects the homozygous wildtype sequence (no insertion in either allele), the heterozygous genotype, or the homozygous insertional genotype.

In any of these circumstances, the medical practitioner "knows" the relevant information that will allow him or her to determine whether a PDE3A inhibitor is an appropriate medicinal option. It is contemplated that, for example, a laboratory conducts the test to determine that patient's genotype such its personnel also know the appropriate information. They may report back to the practitioner with the specific result of the test performed or the laboratory may simply report that a PDE3A inhibitor is an appropriate drug based on the laboratory results. Depending on the result, the patient may be subsequent treated with the PDE3A inhibitor. In certain embodiments, a PDE3A inhibitor such as enoximone is administered to a patient after the patient has been genotyped as having the homozygous wildtype sequence (no insertion in either allele), the heterozygous genotype, or the homozygous insertional genotype. The term "genotyping" is refers to the physical manipulation and transformation of a biological sample to determine genotype information contained in the sample. Obtaining genotype information refers to obtaining some or all of the results of a genotyped sample.

Certain embodiments are directed to a tangible, computer-readable medium comprising a genotype of a subject, wherein the genotype exhibits the presence or absence of a Evi-1 insertion in the PDE3A gene. In certain aspects the medium comprising the genotype of the subject exhibits the presence of a Evi-1 insertion in the promoter of one or more PDE3A gene. Moreover, in further embodiments the medium or method involves an algorithm that determines the risk of a phenotype based on the genotype information. In particular embodiments a method involves a computer specifically programmed to evaluate a genotype result and determine whether a particular PDE3A inhibitor is an appropriate drug. This determination may involve a probability analysis. A report may be subsequently prepared with the results of the genotyping and/or predicted phenotype.

Moreover, in some methods a clinician may or may not order a genotyping test for a patient. In other embodiments, a clinician may retrieve a biological sample from a patient, which may or may not constitute a biopsy. In further embodiments, methods may involve receiving genotype information about a patient's sample and subsequently treating a patient with a PDE3A inhibitor based on the genotype information. In further methods, an algorithm may be run to evaluate possible phenotype based on genotyping information.

As used herein, the term "heart failure" is broadly used to mean any condition that reduces the ability of the heart to pump blood. As a result, congestion and edema develop in the tissues. Most frequently, heart failure is caused by decreased contractility of the myocardium, resulting from reduced coronary blood flow; however, many other factors may result in heart failure, including damage to the heart valves, vitamin deficiency, and primary cardiac muscle disease. Though the precise physiological mechanisms of heart failure are not entirely understood, heart failure is generally believed to involve disorders in several cardiac autonomic properties, including sympathetic, parasympathetic, and baroreceptor responses. The phrase "manifestations of heart failure" is used broadly to encompass all of the sequelae associated with heart failure, such as shortness of breath, pitting edema, an enlarged tender liver, engorged neck veins, pulmonary rates and the like including laboratory findings associated with heart failure.

The term "treatment" or equivalents encompasses the improvement and/or reversal of the symptoms of heart failure (i.e., the ability of the heart to pump blood). "Improvement in the physiologic function" of the heart may be assessed using any of the measurements described herein (e.g., measurement of ejection fraction, fractional shortening, left ventricular internal dimension, heart rate, etc.), as well as any effect upon subject's survival. In certain embodiments, a patient administers the drug to himself/herself.

The term "dilated cardiomyopathy" refers to a type of heart failure characterized by the presence of a symmetrically dilated left ventricle with poor systolic contractile function and, in addition, frequently involves the right ventricle.

As used herein, the term "cardiac hypertrophy" refers to the process in which adult cardiac myocytes respond to stress through hypertrophic growth. Such growth is characterized by cell size increases without cell division, assembling of additional sarcomeres within the cell to attempt to increase force generation, and an activation of a fetal cardiac gene program that inherently reduces myocardial function. Cardiac hypertrophy is often associated with increased risk of morbidity and mortality, and thus studies aimed at understanding the molecular mechanisms of cardiac hypertrophy could have a significant impact on human health.

As used herein, the terms "antagonist" and "inhibitor" refer to molecules, compounds, or nucleic acids which inhibit the action of a protein. Antagonists and inhibitors may include proteins, nucleic acids, carbohydrates, or any other molecules which bind or interact with a protein of interest.

The term "phosphodiesterase inhibitor" or "PDE inhibitor" refers to a chemical compound or entity that is capable of blocking, either partially or completely, the activity of a phosphodiesterase enzyme. Some PDE inhibitors exhibit a degree of specificity for one PDE subtype (e.g., phosphodiesterase type 3A (PDE3A)). The term "PDE3A inhibitor" refers to chemical compounds that are selective for phosphodiesterase type 3A. The use of derivatives of known PDE3A inhibitors is encompassed by the methods of the present invention. Indeed any compound, which functionally behaves as a PDE3A inhibitor is encompassed by the methods of the present invention.

As used herein, the term "genotype" refers to the actual genetic make-up of an organism, while "phenotype" refers to physical traits displayed by an individual (responsiveness to PDE3A inhibitors for the treatment of heart failure).

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The terms "inhibiting," "reducing," or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the teen "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any foam of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
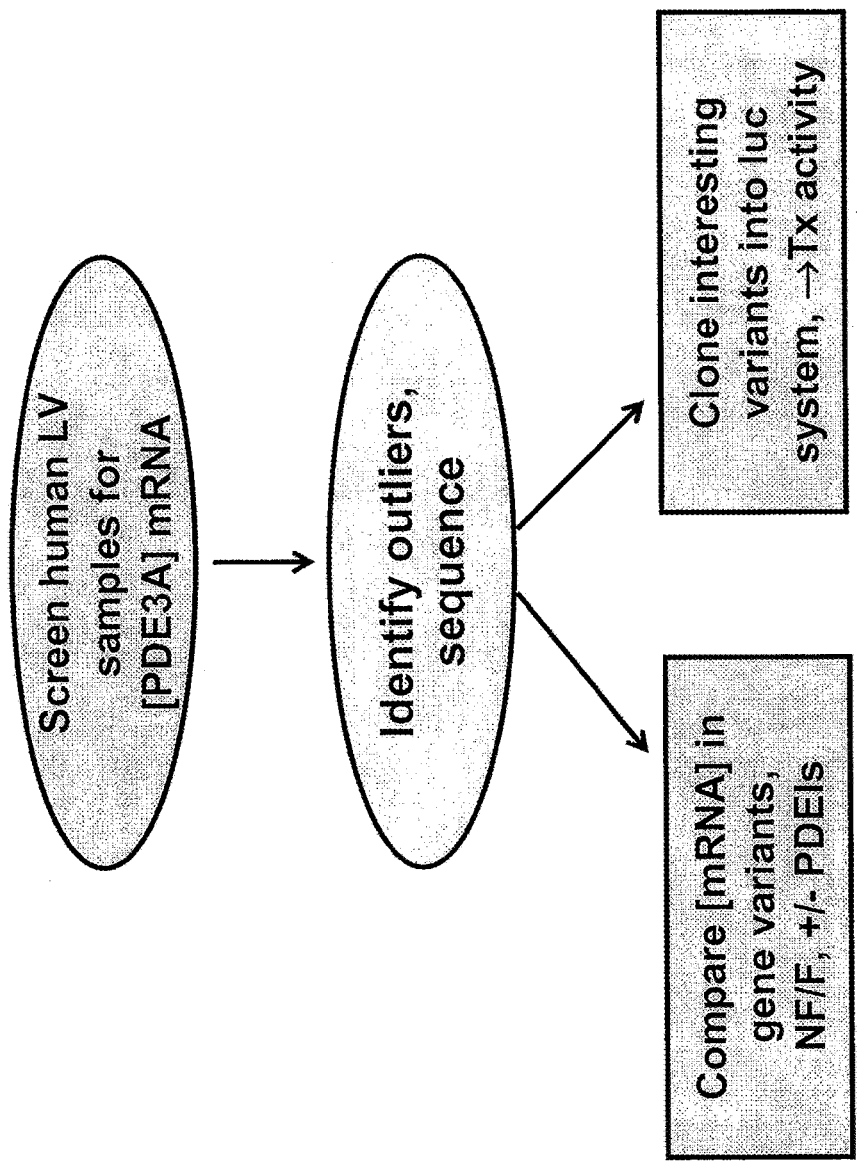
FIG. 1. Scheme for identification of functionally important polymorphisms in the PDE3A gene promoter (no NS SNPs in coding regions).

The present invention relates generally to assessing a PDE3A polymorphism in an individual and to assessing the individual regarding responsiveness to PDE3A inhibitor treatment. Some conditions associated with PDE3A treatment are not advantageous to the individual, for example, some patients develop a tolerance to PDE3A inhibitors. Specifically, the present invention relates to determining the genotype for an individual at the PDE3A gene (e.g., determining if the subject has an insertional polymorphism).

The methods of the invention can also be applied to facilitate the selection of a therapy for conditions in which inhibition of PDE3A can be beneficial. The inhibition of PDE3A can result in an increase in cAMP in the heart and in the phospholamban microdomain. However, providing information to the clinician regarding the propensity of an individual to experience adverse side effects, such as development of tolerance to the inhibitor, is of value in selecting a therapy regimen from which the individual will benefit most and/or with which the patient will most likely comply with a prescribed regimen. Thus, it is of interest to provide a method for assessing the level and propensity for developing tolerance for PDE3A inhibitors in selecting a PDE3A inhibitor based therapy or prescribing an alternate therapy.

Pharmacogenomics allows a clinician or physician to target prophylactic or therapeutic treatments to individuals who will most benefit from the treatment and to avoid treatment of individuals who will experience symptomatic side effects. Transcriptional regulation and feedback down-regulation of transcription can lead to therapeutic failure by altering the quantity of enzymatic target in a tissue. Thus, a physician or clinician may consider applying knowledge obtained in relevant pharmacogenomics studies in determining whether to administer a PDE3A inhibitor as well as tailoring the dosage, regimen, and/or therapeutically effective amounts to be administered so as to attain the effect desired by the treatment.

Heart failure is one of the leading causes of morbidity and mortality in the world. In the U.S. alone, estimates indicate that 3 million people are currently living with cardiomyopathy and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals (Durand et al., 1995). Although there are other causes of DCM, familiar dilated cardiomyopathy has been indicated as representing approximately 20% of "idiopathic" DCM. Approximately half of the DCM cases are idiopathic, with the remainder being associated with known disease processes. For example, serious myocardial damage can result from certain drugs used in cancer chemotherapy (e.g., doxorubicin and daunoribucin). In addition, many DCM patients are chronic alcoholics. Fortunately, for these patients, the progression of myocardial dysfunction may be stopped or reversed if alcohol consumption is reduced or stopped early in the course of disease. Peripartum cardiomyopathy is another idiopathic of DCM, as is disease associated with infectious sequelae. In sum, cardiomyopathies, including DCM, are significant public health problems. Additional methods of improving the outcome of therapy for heart failure are needed. In certain embodiments of the present application are directed to compositions and method for identifying a patient population responsive to PDE3A inhibitor treatment and methods of treating such a population are described.

I. PHOSPHODIESTERASE (PDE)

cAMP signaling plays important roles in both physiologic and pathologic regulation of cardiac performance (Wang and Dhalla, 2000). cAMP is one of the most well characterized signaling molecules in β-AR signaling, but its contribution to Ang II signaling in cardiomyocytes is not fully understood. Clinical and experimental studies indicate that acute stimulation of β-AR/cAMP signaling increases myocyte contractility, which is beneficial. In contrast, chronic stimulation of cAMP signaling promotes myocyte apoptosis, which is harmful to the heart (Wang and Dhalla, 2000). The temporal and spatial features of cAMP production in the cell are controlled by adenylyl cyclases that catalyze the synthesis of cAMP, and phosphodiesterases (PDEs) that hydrolyze cAMP.

Phosphodiesterase as used herein refers to cyclic nucleotide phosphodiesterases. The cyclic nucleotide phosphodiesterases (PDE) comprise a group of enzymes that degrade the phosphodiester bond in the second messenger molecules cAMP and cGMP. They regulate the localization, duration, and amplitude of cyclic nucleotide signaling within subcellular domains. PDEs are therefore important regulators of signal transduction mediated by these second messenger molecules.

PDE enzymes are often targets for pharmacological inhibition due to their unique tissue distribution, structural properties, and functional properties. Inhibitors of PDE can prolong or enhance the effects of physiological processes mediated by cAMP or cGMP by inhibition of their degradation by PDE. For example, Sildenafil (Viagra) is an inhibitor of cGMP specific phosphodiesterase type 5, which enhances the vasodilatory effects of cGMP in the corpus cavernosum and is used to treat erectile dysfunction. Cilostazol (Pletal) inhibits PDE3. This inhibition allows Red Blood Cells to be more able to bend. This is useful in conditions such as intermittent claudication, as the cells can maneuver through constricted veins and arteries more easily.

PDE3 cyclic nucleotide phosphodiesterases bind cAMP and cGMP with high affinity and hydrolyze both substrates in a mutually competitive manner (Shakur et al., 2000). Two PDE3 genes have been discovered: PDE3A is expressed primarily in cardiac and vascular myocytes and platelets, whereas PDE3B is expressed primarily in adipocytes, hepatocytes, and pancreatic cells (Reinhardt et al., 1995). Phosphodiesterase type 3 (PDE3) is an important regulator of cAMP-mediated responses within the cardiovascular system. PDE3 inhibitors (e.g. milrinone and enoximone) have inotropic effects attributable to the elevation of cAMP content in cardiac myocytes and vasodilatory effects attributable to the elevation of cAMP and/or cGMP content in vascular myocytes, and have been used to augment contractility and reduce afterload in patients with dilated cardiomyopathy (Movsesian, 1999). PDE3A is significantly down-regulated in human failing hearts and in a mouse model of chronic pressure overload (Ding et al., 2005). Down-regulation of PDE3A expression/activity induced cardiomyocyte apoptosis in cultured cardiomyocytes, due to PDE3A down-regulation-mediated induction of the proapoptotic transcriptional repressor ICER (Ding et al., 2005).

II. DETECTION OF POLYMORPHISMS

The insertional polymorphism described herein is present in the promoter of PDE3A genes and affect the transcrptional regulation the PDE3A gene. The presence of the insertional polymorphism can be determined from the sequence of the PDE3A promoter or by using specific characteristics of the insertional polymorphism, e.g., amplicon size. As a result, a variety of different methodologies can be employed for the purpose of detecting polymorphisms in the promoter of PDE3A.

The insertional polymorphism comprises a binding site for the transcription factor Evi-1. Evi-1 (Ecotropic viral integration site-1) is a human protein encoded by the Evi-1 gene. The gene was first identified in AKXD murine myeloid tumors. Evi-1 is a nuclear transcription factor involved in many signaling pathways for both corepression and coactivation of various genes. The Evi-1 protein binds to a consensus sequence of DGATADGADWAGATA (SEQ ID NO:5).

A. Nucleic Acids

Certain embodiments of the present invention concern various nucleic acids, including amplification primers, oligonucleotide probes, and other nucleic acid elements involved in the analysis of genomic DNA. In certain aspects, a nucleic acid comprises a wild-type, a mutant, or a polymorphic nucleic acid.

The terms "PDE3A" polymorphism or "PDE3A insertional" polymorphism refer to polymorphisms in the promoter a PDE3A gene. The sequence of the PDE3A promoter segment containing an insertional polymorphism is provided as SEQ ID NO:3. The sequence of the PDE3A promoter segment lacking the insertional polymorphism is provided as SEQ ID NO:4.

For the purposes of identifying the location of a polymorphism, the first nucleotide of a transcription start site is considered nucleotide "+1," i.e., the transcriptional start designated in SEQ ID NO:4 is present at nucleotide 1406 of SEQ ID NO:4. Nucleotide positions in the promoter are typically designated by negative number beginning with first nucleotide before the transcription start site as "4" and decreasing in number as you progress along the PDE3A promoter sequence to the first nucleotide of the sequence represented in the sequence listing. Alternatively, the location of a polymorphism can be designated based on the total number of nucleotides in the sequence starting as nucleotide 1 and progressing in increments of one to the end of the sequence, i.e., nucleotide 1842 of SEQ ID NO:4. Given this convention, the insertion in SEQ ID NO:3 begins at nucleotide 276 and the last nucleotide of the insertion is at nucleotide 304 of SEQ ID NO:3. Thus, the insertion is defined as nucleotides 276-304 of SEQ ID NO:3 (i.e., SEQ ID NO:2). Relative to SEQ ID NO:4 the insertion—an Evi-1 binding site—is inserted after nucleotide 275 of SEQ ID NO:4.

In some embodiments, nucleic acids of the invention comprise or are complementary to all or 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1165, 1200, 1300, 1400, 1500, 1840, 1870 or more contiguous nucleotides, or any range derivable therein, of the human PDE3A promoter segment provided in SEQ ID NO:3 or SEQ ID NO:4. One of skill in the art knows how to design and use primers and probes for hybridization and amplification of the PDE3A promoter.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts."

1. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in European Patent 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. In certain aspects amplification oligonucleotides can be designed on either side or overlapping with the boundaries of the insertion site. In a further aspect an oligonucleotide specific for insertion as compare to the PDE3A promoter laking the insertional polymorphism can be designed. These oligonucleotides can varying in length from 5, 10, 15, 16, 17, 18, 19, 20, 21, 22, 23, 24, 25, 26, 27, 28, 29, 30, 50, nucleotides or more, including all values and ranges there between. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

2. Purification of Nucleic Acids

A nucleic acid may be purified on polyacrylamide gels, cesium chloride centrifugation gradients, chromatography columns or by any other means known to one of ordinary skill in the art (see for example, Sambrook et al., 2001, incorporated herein by reference).

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

3. Nucleic Acid Segments

In certain embodiments, the nucleic acid is a nucleic acid segment. As used herein, the term "nucleic acid segment," are fragments of a nucleic acid, such as, for a non-limiting example, those that encode only part of a PDE3A promoter sequence, or part of the PDE3A gene locus or gene sequence. Thus, a "nucleic acid segment" may comprise any part of a gene sequence, including from about 2 nucleotides to the full length gene including promoter regions to the polyadenylation signal and any length that includes all the coding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

4. Nucleic Acid Complements

The present invention also encompasses a nucleic acid that is complementary to a nucleic acid. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule. In preferred embodiments, a complement is a hybridization probe or amplification primer for the detection of a nucleic acid polymorphism.

As used herein, the term "complementary" or "complement" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. However, in some diagnostic or detection embodiments, completely complementary nucleic acids are preferred.

5. Nucleic Acid Detection and Evaluation

Genotyping can be performed using methods described in Small et al. (2002), which is incorporated herein by reference. It will be understood by the skilled artisan that other standard techniques are available for genotyping and any technique may be used with the present invention. General methods of nucleic acid detection methods are provided below.

One genotyping method involves isolating from the individual a nucleic acid mixture comprising the two copies of the PDE3A gene, or a fragment thereof, that are present in the individual, and determining the nucleotide sequence or presence of a nucleotide insertion in the promoter of the PDE3A gene. Other polymorphisms, such as single nucleotide polymorphisms can be linked to and indicative of the insertional polymorphism described herein.

Those in the art will readily recognize that nucleic acid molecules may be double-stranded molecules and that reference to a particular site on one strand refers, as well, to the corresponding site on a complementary strand. Thus, in defining a polymorphic site, reference to a sequence including an adenine, a thymine (uridine), a cytosine, or a guanine at a particular site on one strand of a nucleic acid molecule is also intended to include the thymine (uridine), adenine, guanine, or cytosine (respectively) at the corresponding site on a complementary strand of a nucleic acid molecule. Thus, reference may be made to either strand and still comprise the same polymorphic site and an oligonucleotide may be designed to hybridize to either strand. Throughout the text, in identifying a polymorphic site, reference is made to SEQ ID NO:3 or SEQ ID NO:4 for the purpose of convenience.

Typically, the nucleic acid mixture is isolated from a biological sample taken from the individual, such as a blood sample or tissue sample using standard techniques such as disclosed in Jones (1963) which is hereby incorporated by reference. Suitable tissue samples include whole blood, semen, saliva, tears, urine, fecal material, sweat, buccal, skin, and hair. The nucleic acid mixture may be comprised of genomic DNA.

The ability to predict a patient's response to a PDE inhibitor is useful for physicians in making decisions about how to treat a patient having heart failure. A patient whose genotype indicates the patient will probably respond well to the PDE inhibitor (i.e., a patient homozygous for a Evi-1 binding site insertional polymorphism) would be a better candidate for PDE inhibitor therapy than a patient who is likely to exhibit tolerance to PDE inhibitor therapy, or an intermediate response, or no response, and the physician would be able to determine with less trial and error which individuals should receive an alternative form of therapy.

In the genotyping methods used in the present invention, the identity of a polymorphic site may be determined by amplifying a target region containing the polymorphic site directly from one or both copies of the PDE3A gene present in the individual and the sequence of the amplified region(s) determined by conventional methods or evaluated directly.

The target region(s) may be amplified using any oligonucleotide-directed amplification method, including but not limited to polymerase chain reaction (PCR) (U.S. Pat. No. 4,965,188), ligase chain reaction (LCR) (Barany et al., 1991; PCT Appln. WO90/01069), and oligonucleotide ligation assay (OLA) (Landegren et al., 1988). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan.

Other known nucleic acid amplification procedures may be used to amplify the target region including transcription-based amplification systems (U.S. Pat. No. 5,130,238; EP 329,822; U.S. Pat. No. 5,169,766, PCT Appln. WO89/06700) and isothermal methods (Walker et al., 1992).

A polymorphism in the target region may also be assayed before or after amplification using one of several hybridization-based methods known in the art. Typically, allele-specific oligonucleotides are utilized in performing such methods. The allele-specific oligonucleotides may be used as differently labeled probe pairs, with one member of the pair showing a perfect match to one variant of a target sequence and the other member showing a perfect match to a different variant. In some embodiments, more than one polymorphic site may be detected at once using a set of allele-specific oligonucleotides or oligonucleotide pairs.

Hybridization of an allele-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Allele-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid.

The genotype for one or more polymorphic sites in the PDE3A gene of an individual may also be determined by hybridization of one or both copies of the gene, or a fragment thereof, to nucleic acid arrays and subarrays such as described in PCT Appln. WO 95/11995. The arrays would contain a battery of allele-specific oligonucleotides representing each of the polymorphic sites to be included in the genotype or haplotype.

The identity of polymorphisms may also be determined using a mismatch detection technique, including but not limited to the RNase protection method using riboprobes (Winter et al., 1985); Meyers et al., 1985) and proteins which recognize nucleotide mismatches, such as the E. coli mutS protein (Modrich, 1991). Alternatively, variant alleles can be identified by single strand conformation polymorphism (SSCP) analysis (Orita et al., 1989; Humphries et al., 1996) or denaturing gradient gel electrophoresis (DGGE) (Wartell et al., 1990; Sheffield et al., 1989).

A polymerase-mediated primer extension method may also be used to identify the polymorphism(s). Several such methods have been described in the patent and scientific literature. Extended primers containing a polymorphism may be detected by mass spectrometry as described in U.S. Pat. No. 5,605,798. An other primer extension method is allele-specific PCR (Ruano et al., 1989; Ruano et al., 1991; PCT Appln. WO 93/22456; Turki et al., 1995).

Polymorphic variation in the promoter of the human PDE3A gene can also be detected using differential digestion of DNA by certain restriction enzymes (Small et al., 2002) or by any other method that identifies the nucleotide insertion in the PDE3A gene.

a. Hybridization

The use of a probe or primer of between 7, 8, 9, 10, 11, 12, 13, 14, 15, 16, 17, 18, 19, 20, 21, 22, 23, 24, 25, 50, 60, 70, 80, 90, or 100 consecutive nucleotides of SEQ ID NO:3 or SEQ ID NO:4, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting a specific polymorphism. It is generally appreciated that conditions can be rendered more stringent by the addition of increasing amounts of formamide. For example, under highly stringent conditions, hybridization to filter-bound DNA may be carried out in 0.5 M $NaHPO_4$, 7% sodium dodecyl sulfate (SDS), 1 mM EDTA at 65° C., and washing in 0.1×SSC/ 0.1% SDS at 68° C. (Ausubel et al., 1989).

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Under low stringent conditions, such as moderately stringent conditions the washing may be carried out for example in 0.2×SSC/ 0.1% SDS at 42° C. (Ausubel et al., 1989). Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples. In other aspects, a particular nuclease cleavage site may be present and detection of a particular nucleotide sequence can be determined by the presence or absence of nucleic acid cleavage.

In general, it is envisioned that the probes or primers described herein will be useful as reagents in solution hybridization, as in PCR, for detection of expression or genotype of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851, 772. The relevant portions of these and other references identified in this section of the Specification are incorporated herein by reference.

b. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples with or without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to the PDE3A gene locus, or variants thereof, and fragments thereof are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected, analyzed or quantified. In certain applications, the detection may be performed by visual means. In certain applications, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Another method for amplification is ligase chain reaction ("LCR"), disclosed in European Appln. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, Great Britain Appln. 2 202 328, and in PCT Application PCT/US89/01025, each of which is incorporated herein by reference in its entirety. Qbeta Replicase, described in PCT Application PCT/US87/00880, may also be used as an amplification method in the present invention.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Appln. WO 88/10315, incorporated herein by reference in their entirety). European Appln. 329 822 disclose a nucleic acid amplification process involving cyclically synthesizing single-stranded RNA ("ssRNA"), ssDNA, and double-stranded DNA (dsDNA), which may be used in accordance with the present invention.

PCT Appln. WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

c. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by spin columns and/or chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

d. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

e. Specific Examples of Polymorphism Nucleic Acid Screening Methods

Spontaneous mutations that arise during the course of evolution in the genomes of organisms are often not immediately transmitted throughout all of the members of the species, thereby creating polymorphic alleles that co-exist in the species populations. Often polymorphisms are the cause of genetic diseases. Several classes of polymorphisms have been identified. For example, variable nucleotide type polymorphisms (VNTRs), arise from spontaneous tandem duplications of di- or trinucleotide repeated motifs of nucleotides. If such variations alter the lengths of DNA fragments generated by restriction endonuclease cleavage, the variations are referred to as restriction fragment length polymorphisms (RFLPs). RFLPs are been widely used in human and animal genetic analyses.

Another class of polymorphisms are generated by the replacement of a single nucleotide. Such single nucleotide polymorphisms (SNPs) rarely result in changes in a restriction endonuclease site. Thus, SNPs are rarely detectable restriction fragment length analysis. SNPs are the most common genetic variations and occur once every 100 to 300 bases and several SNP mutations have been found that affect a single nucleotide in a protein-encoding gene in a manner sufficient to actually cause a genetic disease. SNP diseases are exemplified by hemophilia, sickle-cell anemia, hereditary hemochromatosis, late-onset alzheimer disease etc.

Several methods have been developed to screen polymorphisms and some examples are listed below. The reference of Kwok and Chen (2003) and Kwok (2001) provide overviews of some of these methods; both of these references are specifically incorporated by reference.

SNPs relating to ABCC2 can be characterized by the use of any of these methods or suitable modification thereof. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or any other biochemical interpretation.

(1) DNA Sequencing

The most commonly used method of characterizing a polymorphism is direct DNA sequencing of the genetic locus that flanks and includes the polymorphism. Such analysis can be accomplished using either the "dideoxy-mediated chain termination method," also known as the "Sanger Method" (Sanger et al., 1975) or the "chemical degradation method," also known as the "Maxam-Gilbert method" (Maxam et al., 1977). Sequencing in combination with genomic sequence-specific amplification technologies, such as the polymerase chain reaction may be utilized to facilitate the recovery of the desired genes (Mullis et al., 1986; European Patent Appln. 50,424; European Patent Appln. 84,796, European Patent Appln. 258,017, European Patent Appln. 237,362; European Patent Appln. 201,184; U.S. Pat. Nos. 4,683,202; 4,582,788; and 4,683,194), all of the above incorporated herein by reference.

(2) Exonuclease Resistance

Other methods that can be employed to determine the identity of a nucleotide present at a polymorphic site utilize a specialized exonuclease-resistant nucleotide derivative (U.S. Pat. No. 4,656,127). A primer complementary to an allelic sequence immediately 3'- to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known one can determine the specific nucleotide present in the polymorphic site of the DNA.

(3) Microsequencing Methods

Several other primer-guided nucleotide incorporation procedures for assaying polymorphic sites in DNA have been described (Komher et al., 1989; Sokolov, 1990; Syvanen 1990; Kuppuswamy et al., 1991; Prezant et al., 1992; Ugozzoll et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1990).

(4) Extension in Solution

French Patent 2,650,840 and PCT Appln. WO91/02087 discuss a solution-based method for determining the identity of the nucleotide of a polymorphic site. According to these methods, a primer complementary to allelic sequences immediately 3'- to a polymorphic site is used. The identity of the nucleotide of that site is determined using labeled dideoxynucleotide derivatives which are incorporated at the end of the primer if complementary to the nucleotide of the polymorphic site.

(5) Genetic Bit Analysis or Solid-Phase Extension

PCT Appln. WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

(6) Oligonucleotide Ligation Assay (OLA)

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR have also been described (Nickerson et al., 1990). Here PCR is used to achieve the exponential amplification of target DNA, which is then detected using the OLA.

(7) Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

(8) Invasive Cleavage Reactions

Invasive cleavage reactions can be used to evaluate cellular DNA for a particular polymorphism. A technology called INVADER® employs such reactions (e.g., de Arruda et al., 2002; Stevens et al., 2003, which are incorporated by reference). Generally, there are three nucleic acid molecules: 1) an oligonucleotide upstream of the target site ("upstream oligo"), 2) a probe oligonucleotide covering the target site ("probe"), and 3) a single-stranded DNA with the target site ("target"). The upstream oligo and probe do not overlap but they contain contiguous sequences. The probe contains a donor fluorophore, such as fluorescein, and an acceptor dye, such as Dabcyl. The nucleotide at the 3' terminal end of the upstream oligo overlaps ("invades") the first base pair of a probe-target duplex. Then the probe is cleaved by a structure-specific 5' nuclease causing separation of the fluorophore/quencher pair, which increases the amount of fluorescence that can be detected. See Lu et al., 2004.

In some cases, the assay is conducted on a solid-surface or in an array format.

(9) Other Methods to Detect SNPs

Several other specific methods for polymorphism detection and identification are presented below and may be used as such or with suitable modifications in conjunction with identifying polymorphisms of the PDE3A gene in the present invention. Several other methods are also described on the SNP web site of the NCBI on the World Wide Web at ncbi.nlm.nih.gov/SNP, incorporated herein by reference.

In a particular embodiment, extended haplotypes may be determined at any given locus in a population, which allows one to identify exactly which SNPs will be redundant and which will be essential in association studies. The latter is referred to as 'haplotype tag SNPs (htSNPs)', markers that capture the haplotypes of a gene or a region of linkage disequilibrium. See Johnson et al. (2001) and Ke and Cardon (2003), each of which is incorporated herein by reference, for exemplary methods.

The VDA-assay utilizes PCR amplification of genomic segments by long PCR methods using TaKaRa LA Taq reagents and other standard reaction conditions. The long amplification can amplify DNA sizes of about 2,000-12,000 bp. Hybridization of products to variant detector array (VDA) can be performed by a Affymetrix High Throughput Screening Center and analyzed with computerized software.

A method called Chip Assay uses PCR amplification of genomic segments by standard or long PCR protocols. Hybridization products are analyzed by VDA, Halushka et al. (1999), incorporated herein by reference. SNPs are generally classified as "Certain" or "Likely" based on computer analysis of hybridization patterns. By comparison to alternative detection methods such as nucleotide sequencing, "Certain" SNPs have been confirmed 100% of the time; and "Likely" SNPs have been confirmed 73% of the time by this method.

Other methods simply involve PCR amplification following digestion with the relevant restriction enzyme. Yet others involve sequencing of purified PCR products from known genomic regions.

In yet another method, individual exons or overlapping fragments of large exons are PCR-amplified. Primers are designed from published or database sequences and PCR-amplification of genomic DNA is performed using the following conditions: 200 ng DNA template, 0.5 µM each primer, 80 µM each of dCTP, dATP, dTTP and dGTP, 5% formamide, 1.5 mM MgCl$_2$, 0.5 U of Taq polymerase and 0.1 volume of the Taq buffer. Thermal cycling is performed and resulting PCR-products are analyzed by PCR-single strand conformation polymorphism (PCR-SSCP) analysis, under a variety of conditions, e.g, 5 or 10% polyacrylamide gel with 15% urea, with or without 5% glycerol. Electrophoresis is performed overnight. PCR-products that show mobility shifts are reamplified and sequenced to identify nucleotide variation.

In a method called CGAP-GAI (DEMIGLACE), sequence and alignment data (from a PHRAP.ace file), quality scores for the sequence base calls (from PHRED quality files), distance information (from PHYLIP dnadist and neighbour programs) and base-calling data (from PHRED '-d' switch) are loaded into memory. Sequences are aligned and examined for each vertical chunk ('slice') of the resulting assembly for disagreement. Any such slice is considered a candidate SNP (DEMIGLACE). A number of filters are used by DEMIGLACE to eliminate slices that are not likely to represent true polymorphisms. These include filters that: (i) exclude sequences in any given slice from SNP consideration where neighboring sequence quality scores drop 40% or more; (ii) exclude calls in which peak amplitude is below the fifteenth percentile of all base calls for that nucleotide type; (iii) disqualify regions of a sequence having a high number of disagreements with the consensus from participating in SNP calculations; (iv) removed from consideration any base call with an alternative call in which the peak takes up 25% or more of the area of the called peak; (v) exclude variations that occur in only one read direction. PHRED quality scores were converted into probability-of-error values for each nucleotide in the slice. Standard Baysian methods are used to calculate the posterior probability that there is evidence of nucleotide heterogeneity at a given location.

In a method called CU-RDF (RESEQ), PCR amplification is performed from DNA isolated from blood using specific primers for each SNP, and after typical cleanup protocols to remove unused primers and free nucleotides, direct sequencing using the same or nested primers.

In a method called DEBNICK (METHOD-B), a comparative analysis of clustered EST sequences is performed and confirmed by fluorescent-based DNA sequencing. In a related method, called DEBNICK (METHOD-C), comparative analysis of clustered EST sequences with phred quality >20 at the site of the mismatch, average phred quality >=20 over 5 bases 5'-FLANK and 3' to the SNP, no mismatches in 5 bases 5' and 3' to the SNP, at least two occurrences of each allele is performed and confirmed by examining traces.

In a method identified by ERO (RESEQ), new primers sets are designed for electronically published STSs and used to amplify DNA from 10 different mouse strains. The amplification product from each strain is then gel purified and sequenced using a standard dideoxy, cycle sequencing technique with $^{33}$P-labeled terminators. All the ddATP terminated reactions are then loaded in adjacent lanes of a sequencing gel followed by all of the ddGTP reactions and so on. SNPs are identified by visually scanning the radiographs.

In another method identified as ERO (RESEQ-HT), new primers sets are designed for electronically published murine DNA sequences and used to amplify DNA from 10 different mouse strains. The amplification product from each strain is prepared for sequencing by treating with Exonuclease I and Shrimp Alkaline Phosphatase. Sequencing is performed using ABI Prism Big Dye Terminator Ready Reaction Kit (Perkin-Elmer) and sequence samples are run on the 3700 DNA Analyzer (96 Capillary Sequencer).

FGU-CBT (SCA2-SNP) identifies a method where the region containing the SNP were PCR amplified using the primers SCA2-FP3 and SCA2-RP3. Approximately 100 ng of genomic DNA is amplified in a 50 ml reaction volume containing a final concentration of 5 mM Tris, 25 mM KCl, 0.75 mM $MgCl_2$, 0.05% gelatin, 20 pmol of each primer and 0.5 U of Taq DNA polymerase. Samples are denatured, annealed and extended and the PCR product is purified from a band cut out of the agarose gel using, for example, the QIAquick gel extraction kit (Qiagen) and is sequenced using dye terminator chemistry on an ABI Prism 377 automated DNA sequencer with the PCR primers.

In a method identified as JBLACK (SEQ/RESTRICT), two independent PCR reactions are performed with genomic DNA. Products from the first reaction are analyzed by sequencing, indicating a unique FspI restriction site. The mutation is confirmed in the product of the second PCR reaction by digesting with Fsp I.

In a method described as KWOK(1), SNPs are identified by comparing high quality genomic sequence data from four randomly chosen individuals by direct DNA sequencing of PCR products with dye-terminator chemistry (see Kwok et al., 1996). In a related method identified as KWOK(2) SNPs are identified by comparing high quality genomic sequence data from overlapping large-insert clones such as bacterial artificial chromosomes (BACs) or P1-based artificial chromosomes (PACs). An STS containing this SNP is then developed and the existence of the SNP in various populations is confirmed by pooled DNA sequencing (see Taillon-Miller et al., 1998). In another similar method called KWOK (3), SNPs are identified by comparing high quality genomic sequence data from overlapping large-insert clones BACs or PACs. The SNPs found by this approach represent DNA sequence variations between the two donor chromosomes but the allele frequencies in the general population have not yet been determined. In method KWOK(5), SNPs are identified by comparing high quality genomic sequence data from a homozygous DNA sample and one or more pooled DNA samples by direct DNA sequencing of PCR products with dye-terminator chemistry. The STSs used are developed from sequence data found in publicly available databases. Specifically, these STSs are amplified by PCR against a complete hydatidiform mole (CHM) that has been shown to be homozygous at all loci and a pool of DNA samples from 80 CEPH parents (see Kwok et al., 1994).

In another such method, KWOK (OverlapSnpDetectionWithPolyBayes), SNPs are discovered by automated computer analysis of overlapping regions of large-insert human genomic clone sequences. For data acquisition, clone sequences are obtained directly from large-scale sequencing centers. This is necessary because base quality sequences are not present/available through GenBank. Raw data processing involves analyzed of clone sequences and accompanying base quality information for consistency. Finished ('base perfect', error rate lower than 1 in 10,000 bp) sequences with no associated base quality sequences are assigned a uniform base quality value of 40 (1 in 10,000 bp error rate). Draft sequences without base quality values are rejected. Processed sequences are entered into a local database. A version of each sequence with known human repeats masked is also stored. Repeat masking is performed with the program "MASKERAID." Overlap detection: Putative overlaps are detected with the program "WUBLAST." Several filtering steps followed in order to eliminate false overlap detection results, i.e. similarities between a pair of clone sequences that arise due to sequence duplication as opposed to true overlap. Total length of overlap, overall percent similarity, number of sequence differences between nucleotides with high base quality value "high-quality mismatches." Results are also compared to results of restriction fragment mapping of genomic clones at Washington University Genome Sequencing Center, finisher's reports on overlaps, and results of the sequence contig building effort at the NCBI. SNP detection: Overlapping pairs of clone sequence are analyzed for candidate SNP sites with the 'POLYBAYES' SNP detection software. Sequence differences between the pair of sequences are scored for the probability of representing true sequence variation as opposed to sequencing error. This process requires the presence of base quality values for both sequences. High-scoring candidates are extracted. The search is restricted to substitution-type single base pair variations. Confidence score of candidate SNP is computed by the POLYBAYES software.

In method identified by KWOK (TaqMan assay), the TaqMan assay is used to determine genotypes for 90 random individuals. In method identified by KYUGEN(Q1), DNA samples of indicated populations are pooled and analyzed by PLACE-SSCP. Peak heights of each allele in the pooled analysis are corrected by those in a heterozygote, and are subsequently used for calculation of allele frequencies. Allele frequencies higher than 10% are reliably quantified by this method. Allele frequency=0 (zero) means that the allele was found among individuals, but the corresponding peak is not seen in the examination of pool. Allele frequency=0-0.1 indicates that minor alleles are detected in the pool but the peaks are too low to reliably quantify.

In yet another method identified as KYUGEN (Method1), PCR products are post-labeled with fluorescent dyes and analyzed by an automated capillary electrophoresis system under SSCP conditions (PLACE-SSCP). Four or more individual DNAs are analyzed with or without two pooled DNA (Japanese pool and CEPH parents pool) in a series of experiments. Alleles are identified by visual inspection. Individual DNAs with different genotypes are sequenced and SNPs identified. Allele frequencies are estimated from peak heights in the pooled samples after correction of signal bias using peak heights in heterozygotes. For the PCR primers are tagged to have 5'-ATT or 5'-GTT at their ends for post-labeling of both strands. Samples of DNA (10 ng/ul) are amplified in reaction mixtures containing the buffer (10 mM Tris-HCl, pH 8.3 or 9.3, 50 mM KCl, 2.0 mM $MgCl_2$), 0.25 µM of each primer, 200 µM of each dNTP, and 0.025 units/µl of Taq DNA polymerase premixed with anti-Taq antibody. The two strands of PCR products are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. For the SSCP: an aliquot of fluorescently labeled PCR products and TAMRA-labeled internal markers are added to deionized formamide, and denatured. Electrophoresis is performed in a capillary using an ABI Prism 310 Genetic Analyzer. Genescan softwares (P-E Biosystems) are used for data collection and data processing. DNA of individuals (two to eleven) including those who showed different genotypes on SSCP are subjected for direct sequencing using big-dye terminator chemistry, on ABI Prism 310 sequencers. Multiple sequence trace files obtained from ABI Prism 310 are processed and aligned by Phred/Phrap and viewed using Consed viewer. SNPs are identified by PolyPhred software and visual inspection.

In yet another method identified as KYUGEN (Method2), individuals with different genotypes are searched by denaturing HPLC (DHPLC) or PLACE-SSCP (Inazuka et al., 1997) and their sequences are determined to identify SNPs. PCR is performed with primers tagged with 5'-ATT or 5'-GTT at their ends for post-labeling of both strands. DHPLC analysis is carried out using the WAVE DNA fragment analysis system (Transgenomic). PCR products are injected into DNASep column, and separated under the conditions determined using WAVEMaker program (Transgenomic). The two strands of PCR products that are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. SSCP followed by electrophoresis is performed in a capillary using an ABI Prism 310 Genetic Analyzer. Genescan softwares (P-E Biosystems). DNA of individuals including those who showed different genotypes on DHPLC or SSCP are subjected for direct sequencing using big-dye terminator chemistry, on ABI Prism 310 sequencer. Multiple sequence trace files obtained from ABI Prism 310 are processed and aligned by Phred/Phrap and viewed using Consed viewer. SNPs are identified by PolyPhred software and visual inspection. Trace chromatogram data of EST sequences in Unigene are processed with PHRED. To identify likely SNPs, single base mismatches are reported from multiple sequence alignments produced by the programs PHRAP, BRO and POA for each Unigene cluster. BRO corrected possible misreported EST orientations, while POA identified and analyzed non-linear alignment structures indicative of gene mixing/chimeras that might produce spurious SNPs. Bayesian inference is used to weigh evidence for true polymorphism versus sequencing error, misalignment or ambiguity, misclustering or chimeric EST sequences, assessing data such as raw chromatogram height, sharpness, overlap and spacing; sequencing error rates; context-sensitivity; cDNA library origin, etc.

In method identified as MARSHFIELD(Method-B), overlapping human DNA sequences which contained putative insertion/deletion polymorphisms are identified through searches of public databases. PCR primers which flanked each polymorphic site are selected from the consensus sequences. Primers are used to amplify individual or pooled human genomic DNA. Resulting PCR products are resolved on a denaturing polyacrylamide gel and a PhosphorImager is used to estimate allele frequencies from DNA pools.

f. Linkage Disequilibrium

Polymorphisms in linkage disequilibrium with another polymorphism in which identification of one polymorphism is predictive of the identity of the linked polymorphism. "Linkage disequilibrium" ("LD" as used herein, though also referred to as "LED" in the art) refers to a situation where a particular combination of alleles (i.e., a variant form of a given gene) or polymorphisms at two loci appears more frequently than would be expected by chance. "Significant" as used in respect to linkage disequilibrium, as determined by one of skill in the art, is contemplated to be a statistical p or α value that may be 0.25 or 0.1 and may be 0.1, 0.05, 0.001, 0.00001 or less. Insertions/deletions in the PDE3A promoter may be determined by evaluating the nucleic acid sequence of a polymorphism in linkage disequilibrium with the insertion/deletion. The invention may be implemented in this manner with respect to one or more polymorphisms so as to allow haplotype analysis. "Haplotype" is used according to its plain and ordinary meaning to one skilled in the art. It refers to a collective genotype of two or more alleles or polymorphisms along one of the homologous chromosomes.

The term "polymorphism", as used herein, refers to a difference in the nucleotide or amino acid sequence of a given nucleotide or amino acid region as compared to a nucleotide or amino acid sequence in the corresponding region of another individual of the same species. Preferably, the species is human. A polymorphism is generally defined in relation to a "reference" sequence. In the subject application, "reference" sequence and "wild type" sequence are used interchangeably. Nucleotide polymorphisms include single nucleotide differences, differences in sequence of more than one nucleotide, and single or multiple nucleotide insertions, inversions, substitutions, and deletions. Amino acid polymorphisms include single amino acid differences, differences in sequence of more than one amino acid, and single or multiple amino acid insertions, substitutions, and deletions.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term biological sample encompasses a clinical sample, and also includes cells in culture, cell supernatants, cell lysates, serum, plasma, biological fluid, and tissue samples. In one embodiment, the sample is collected by the individual. For example, an individual can collect a swap of tissue from the inside of the cheek for use as a nucleic acid sample. As known in the art, many types of samples can be used for the extraction of nucleic acids.

As used herein the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder. Treatment, as used in this context, covers any treatment of a symptomatic condition, such as an adverse reaction in a mammal, particularly in a human, and includes: (a) diagnosing and then preventing the adverse reaction from occurring in an individual which can be predisposed to the reaction but has not yet been diagnosed as having it; (b) inhibiting the adverse reaction, i.e., arresting its development; and (c) relieving the adverse reaction, i.e., causing regression of the reaction.

The term "therapeutically effective amount" means an amount that is effective in treating a particular disorder; that is an amount that is effective for reducing the severity of one or more symptoms associated with the particular disorder for which treatment is sought. The term "ameliorate," as used for instance in the amelioration of a particular condition means to make one or more symptoms of the condition at least more tolerable, if not better. The term ameliorate does not necessarily mean an increase in toleration of all symptoms associated with a disorder and does not necessarily mean a complete reduction in the severity of one or more symptoms associated with a disorder.

In another embodiment, a further step is added wherein a portion of the PDE3A gene spanning nucleotides 274 to 302 of SEQ ID NO:3 is amplified prior to the identifying step. In another embodiment, the identifying is performed by a method selected from the group consisting of a hybridization assay, a sequencing assay, a microsequencing assay, a MALDI-TOF assay, and an allele-specific amplification assay. In a further embodiment, the identifying is performed by an antibody-based assay.

Pharmacogenomics allows a clinician or physician to target prophylactic or therapeutic treatments to individuals who will most benefit from the treatment and to avoid treatment of individuals who will experience symptomatic side effects, in the case of a PDE3A inhibitor the adverse side effect can be tolerance and toxicity to the PDE3A inhibitor. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a PDE3A inhibitor as well as tailoring the dosage, regimen, and/or therapeutically effective amounts to be administered so as to attain the effect desired by treatment with the modulator.

A determination of how a given PDE3A polymorphism is predictive of an individual's likelihood of responding to a given drug treatment for a condition relating to abnormally high levels of circulating lipids can be accomplished by determining the genotype of the individual in the PDE3A gene, as described above. Information generated from one or more of these approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating an individual with a niacin receptor modulator, such as niacin or an analog thereof.

In one embodiment, the invention provides a kit for use in the methods of the invention, for example, a kit for determining a level of probability for an individual for a condition responsiveness to PDE3A therapy, a kit for using a PDE3A zygosity of an individual for determining a suitability or an unsuitability of an individual for inclusion in a clinical trial, or a kit for determining a level of probability for a condition associated with heart failure. A kit can comprise reagents and instructions for performing the methods of the invention. For example, a kit can include genotyping reagents such as reagents for isolating nucleic acid molecules and reagents for amplifying nucleic acid molecules such as primers. A kit can also include, for example, a PDE3A assay such as an ELISA. In addition, a kit can contain control samples, for example, to show that amplification reactions are not contaminated.

The contents of the kit are contained in packaging material, preferably to provide a sterile, contaminant-free environment. In addition, the packaging material contains instructions indicating how the materials within the kit can be employed. The instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

III. METHODS OF TREATING CARDIAC HYPERTROPHY

Once the PDE3A genotype of the individual is determined a therapeutic course of treatment may be individualized. In a preferred embodiment of the method, the trait of interest is a clinical response exhibited by a patient to some therapeutic treatment, for example, response to a drug such as but not limited to a PDE3A inhibitor. The term "clinical response" means a quantitative measure of the efficacy or potency of the therapy and adverse events (i.e., side effects).

Thus, individuals homozygous for an insertional polymorphism in the PDE3A gene having or suspected of having or at risk of developing heart failure can be placed on a therapy that includes PDE3A inhibitors such as but not limited to enoximone. The PDE3A inhibitor may be administered alone or in combination with at least one other agent, such as a stabilizing compound.

A. Routes of Administration

Administration of the PDE3A inhibitor may be by any number of routes including, but not limited to oral, intravenous, intramuscular, intra-arterial, intramedullary, intrathecal, intraventricular, intradermal, intratracheal, intravesicle, intraocular, transdermal, subcutaneous, intraperitoneal, intranasal, enteral, topical, sublingual, or rectal. Further details on techniques for formulation and administration may be found in the latest edition of Remington's Pharmaceutical Sciences (Maack Publishing Co., Easton, Pa.). In certain embodiments enoximone or other PDE3A inhibitors are formulated for oral administration.

B. Formulations

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

Aqueous compositions of the present invention comprise an effective amount of the agent, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

1. Controlled/Extended/Sustained/Prolonged Release Administration

Another aspect of this invention provides methods of treating heart failure patients by delivering a PDE3A inhibitor to a patient, having a homozygous insertional polymorhism genotype, as a controlled release formulation. As used herein, the terms "controlled," "extended," "sustained," or "prolonged" release of the composition of the present invention will collectively be referred to herein as "controlled release," and includes continuous or discontinuous, and linear or non-linear release of the composition of the present invention.

a. Tablets

A controlled release tablet suitable for purposes of this invention is disclosed in U.S. Pat. No. 5,126,145, which is incorporated by reference herein. This tablet comprises, in admixture, about 5-30% high viscosity hydroxypropyl methyl cellulose, about 2-15% of a water-soluble pharmaceutical binder, about 2-20% of a hydrophobic component such as a waxy material, e.g., a fatty acid, and about 30-90% active ingredient.

b. Films

This invention further provides a prophylaxis for or method of treating a patient having a homozygous insertional polymorphism in the PDE3A gene following an invasive cardiac procedure comprising administering biodegradable, biocompatible polymeric film comprising a PDE3A inhibitor, such as enoximone, to a patient. The polymeric films are thin compared to their length and breadth. The films typically have a uniform selected thickness between about 60 micrometers and about 5 mm. Films of between about 600 micrometers and 1 mm and between about 1 mm and about 5 mm thick, as well as films between about 60 micrometers and about 1000 micrometers, and between about 60 and about 300 micrometers are useful in the manufacture of therapeutic implants for insertion into a patient's body. The films can be administered to the patient in a manner similar to methods used in adhesion surgeries. For example, a PDE3A inhibitor film formulation can be sprayed or dropped onto a cardiac tissue site or artery during surgery, or a formed film can be placed over the selected tissue site. In an alternative embodiment, the film can be used as controlled release coating on a medical device such as a stent, as is discussed in further detail below.

Either biodegradable or nonbiodegradable polymers may be used to fabricate implants in which the PDE3A inhibitor is uniformly distributed throughout the polymer matrix. A number of suitable biodegradable polymers for use in making the biodegradable films of this invention are known to the art, including polyanhydrides and aliphatic polyesters, preferably polylactic acid (PLA), polyglycolic acid (PGA) and mixtures and copolymers thereof, more preferably 50:50 copolymers of PLA:PGA and most preferably 75:25 copolymers of PLA:PGA. Single enantiomers of PLA may also be used, preferably L-PLA, either alone or in combination with PGA. Polycarbonates, polyfumarates and caprolactones may also be used to make the implants of this invention.

The amount of the PDE3A inhibitor to be incorporated into the polymeric films of this invention is an amount effective to show a measurable effect in treating diseases having similar pathophysiological states, such as but not limited to heart failure. The composition of the present invention can be incorporated into the film by various techniques such as by solution methods, suspension methods, or melt pressing.

c. Transdermal Patch Device

Transdermal delivery involves delivery of a therapeutic agent through the skin for distribution within the body by circulation of the blood. Transdermal delivery can be compared to continuous, controlled intravenous delivery of a drug using the skin as a port of entry instead of an intravenous needle. The therapeutic agent passes through the outer layers of the skin, diffuses into the capillaries or tiny blood vessels in the skin and then is transported into the main circulatory system.

Transdermal patch devices which provide a controlled, continuous administration of a therapeutic agent through the skin are well known in the art. Such devices, for example, are disclosed in U.S. Pat. Nos. 4,627,429; 4,784,857; 5,662,925; 5,788,983; and 6,113,940, which are all incorporated herein by reference. Characteristically, these devices contain a drug impermeable backing layer which defines the outer surface of the device and a permeable skin attaching membrane, such as an adhesive layer, sealed to the barrier layer in such a way as to create a reservoir between them in which the therapeutic agent is placed. In one embodiment of the present invention, a formulation of the PDE3A inhibitor is introduced into the reservoir of a transdermal patch and used by a patient who is homozygous for an insertional polymorphism at the PDE3A gene.

d. Medical Devices

Another embodiment contemplates the incorporation of a PDE3A inhibitor into a medical device that is then positioned to a desired target location within the body, whereupon the PDE3A inhibitor elutes from the medical device. As used herein, "medical device" refers to a device that is introduced temporarily or permanently into a mammal for the prophylaxis or therapy of a medical condition. These devices include any that are introduced subcutaneously, percutaneously or surgically to rest within an organ, tissue or lumen. Medical devices include, but are not limited to, stents, synthetic grafts, artificial heart valves, artificial hearts and fixtures to connect the prosthetic organ to the vascular circulation, venous valves, abdominal aortic aneurysm (AAA) grafts, inferior venal caval filters, catheters including permanent drug infusion catheters, embolic coils, embolic materials used in vascular embolization (e.g., PVA foams), mesh repair materials, a Dracon vascular particle orthopedic metallic plates, rods and screws and vascular sutures.

In one embodiment, the medical device such as a stent or graft is coated with a matrix. The matrix used to coat the stent or graft according to this invention may be prepared from a variety of materials. A primary requirement for the matrix is that it be sufficiently elastic and flexible to remain unruptured on the exposed surfaces of the stent or synthetic graft.

B. Dosages

The amount of PDE3A inhibitor (e.g., enoximone) that is administered or prescribed to the patient can be about, at least about, or at most about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg, or any range derivable therein. This may be with respect to a single dose or total dose in a day (24 hour period) or in a week. Alternatively, the amount administered or prescribed may be about, at least about, or at most about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0 mg/kg, or any range derivable therein, with respect to the weight of the patient.

When provided in a discrete amount, each intake of PDE3A inhibitor can be considered a "dose." A medical practitioner may prescribe or administer multiple doses of PDE3A inhibitor over a particular time course (treatment regimen) or indefinitely.

PDE3A inhibitor may be prescribed or administered 1, 2, 3, 4, 5, 6, 7, 8, 9, 10, 11, 12, 13, 14, 15, 16, 17, 18, 19, 20, 30, 40, 50, 60, 70, 80, or more times or any range derivable therein. It is further contemplated that the drug may be taken for an indefinite period of time or for as long as the patient exhibits symptoms of the medical condition for which PDE3A inhibitor was prescribed or administered. Also, the drug may be administered every 2, 3, 4, 5, 6, 7, 8, 9, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months or more, or any range derivable therein. Alternatively, it may be administered systemically over any such period of time and be extended beyond more than a year. Alternatively, a patient may be treated 1, 2, 3, 4, 5, or 6 times a day with the same or different doses. In some cases, the dose is up-titrated or down-titrated.

C. Other Therapeutic Options

In certain embodiments of the invention, methods may involve administering a PDE3A inhibitor that is not enoximnoe or that is a diuretic, ACE-I, AII antagonist, BNP, $Ca^{++}$-blocker, or an HDAC inhibitor. These agents may be prescribed or administered instead of or in addition to a PDE3A inhibitor after the PDE3A polymorphisms are evaluated.

As a second therapeutic regimen, the agent may be administered or taken at the same time as a PDE3A inhibitor, or either before or after a PDE3A inhibitor. The treatment may improve one or more symptoms of pathologic cardiac hypertrophy or heart failure such as providing increased exercise capacity, increased cardiac ejection volume, decreased left ventricular end diastolic pressure, decreased pulmonary capillary wedge pressure, increased cardiac output or cardiac index, lowered pulmonary artery pressures, decreased left ventricular end systolic and diastolic dimensions, decreased left and right ventricular wall stress, decreased wall tension and wall thickness, increased quality of life, and decreased disease-related morbidity and mortality.

In another embodiment, it is envisioned to use a PDE3A inhibitor in combination with other therapeutic modalities. Thus, in addition to the therapies described above, one may also provide to the patient more "standard" pharmaceutical cardiac therapies. Examples of other therapies include, without limitation, beta blockers, anti-hypertensives, cardiotonics, anti-thrombotics, vasodilators, hormone antagonists, iontropes, diuretics, endothelin antagonists, calcium channel blockers, phosphodiesterase inhibitors, ACE inhibitors, angiotensin type 2 antagonists and cytokine blockers/inhibitors, and HDAC inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the therapy using a PDE3A inhibitor may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either a PDE3A inhibitor, or the other agent will be desired. In this regard, various combinations may be employed. By way of illustration, where the PDE3A inhibitor is "A" and the other agent is "B", the following permutations based on 3 and 4 total administrations are exemplary:

| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are likewise contemplated.

1. Pharmacological Therapeutic Agents

Pharmacological therapeutic agents and methods of administration, dosages, etc., are well known to those of skill in the art (see for example, the "Physicians Desk Reference", Klaassen's "The Pharmacological Basis of Therapeutics", "Remington's Pharmaceutical Sciences", and "The Merck Index, Eleventh Edition", incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such individual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

a. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

(1) Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

(2) Resins/Bile Acid Sequesterants

Non-limiting examples of resins/bile acid sequesterants include cholestyramine (cholybar, questran), colestipol (colestid) and polidexide.

(3) HMG CoA Reductase Inhibitors

Non-limiting examples of HMG CoA reductase inhibitors include lovastatin (mevacor), pravastatin (pravochol) or simvastatin (zocor).

(4) Nicotinic Acid Derivatives

Non-limiting examples of nicotinic acid derivatives include nicotinate, acepimox, niceritrol, nicoclonate, nicomol and oxiniacic acid.

(5) Thyroid Hormones and Analogs

Non-limiting examples of thyroid hormones and analogs thereof include etoroxate, thyropropic acid and thyroxine.

(6) Miscellaneous Antihyperlipoproteinemics

Non-limiting examples of miscellaneous antihyperlipoproteinemics include acifran, azacosterol, benfluorex, β-benzalbutyramide, carnitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, γ-oryzanol, pantethine, pentaerythritol tetraacetate, α-phenylbutyramide, pirozadil, probucol (lorelco), β-sitosterol, sultosilic acid-piperazine salt, tiadenol, triparanol and xenbucin.

b. Antiarteriosclerotics

Non-limiting examples of an antiarteriosclerotic include pyridinol carbamate.

c. Antithrombotic/Fibrinolytic Agents

In certain embodiments, administration of an agent that aids in the removal or prevention of blood clots may be combined with administration of a modulator, particularly in treatment of athersclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

(1) Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

(2) Antiplatelet Agents

Non-limiting examples of antiplatelet agents include aspirin, a dextran, dipyridamole (persantin), heparin, sulfinpyranone (anturane) and ticlopidine (ticlid).

(3) Thrombolytic Agents

Non-limiting examples of thrombolytic agents include tissue plaminogen activator (activase), plasmin, pro-urokinase, urokinase (abbokinase) streptokinase (streptase), anistreplase/APSAC (eminase).

d. Blood Coagulants

In certain embodiments wherein a patient is suffering from a hemmorage or an increased likelihood of hemmoraging, an agent that may enhance blood coagulation may be used. Non-limiting examples of a blood coagulation promoting agent include thrombolytic agent antagonists and anticoagulant antagonists.

(1) Anticoagulant Antagonists

Non-limiting examples of anticoagulant antagonists include protamine and vitamine K1.

(2) Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

e. Antiarrhythmic Agents

Non-limiting examples of antiarrhythmic agents include Class I antiarrythmic agents (sodium channel blockers), Class II antiarrythmic agents (beta-adrenergic blockers), Class II antiarrythmic agents (repolarization prolonging drugs), Class IV antiarrhythmic agents (calcium channel blockers) and miscellaneous antiarrythmic agents.

(1) Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocaine), tocainide (tonocard) and mexiletine (mexitil). Non-limiting examples of Class IC antiarrhythmic agents include encainide (enkaid) and flecamide (tambocor).

(2) Beta Blockers

Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

(3) Repolarization Prolonging Agents

Non-limiting examples of an agent that prolong repolarization, also known as a Class III antiarrhythmic agent, include amiodarone (cordarone) and sotalol (betapace).

(4) Calcium Channel Blockers/Antagonist

Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a miscellaneous calcium channel blocker such as bencyclane, etafenone, magnesium, mibefradil or perhexyline. In certain embodiments a calcium channel blocker comprises a long-acting dihydropyridine (nifedipine-type) calcium antagonist.

(5) Miscellaneous Antiarrhythmic Agents

Non-limiting examples of miscellaneous antiarrhymic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

f. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

(1) Alpha Blockers

Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

(2) Alpha/Beta Blockers

In certain embodiments, an antihypertensive agent is both an alpha and beta adrenergic antagonist. Non-limiting examples of an alpha/beta blocker comprise labetalol (normodyne, trandate).

(3) Anti-Angiotension II Agents

Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

(4) Sympatholytics

Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

(5) Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimefylline, trapidil, tricromyl, trimetazidine, trolnitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

(6) Miscellaneous Antihypertensives

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a sulfonamide derivative.

Arylethanolamine Derivatives.

Non-limiting examples of arylethanolamine derivatives include amosulalol, bufuralol, dilevalol, labetalol, pronethalol, sotalol and sulfinalol.

Benzothiadiazine Derivatives.

Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

N-Carboxyalkyl(Peptide/Lactam) Derivatives.

Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives.

Non-limiting examples of dihydropyridine derivatives include amlodipine, felodipine, isradipine, nicardipine, nifedipine, nilvadipine, nisoldipine and nitrendipine.

Guanidine Derivatives.

Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines.

Non-limiting examples of hydrazines/phthalazines include budralazine, cadralazine, dihydralazine, endralazine, hydracarbazine, hydralazine, pheniprazine, pildralazine and todralazine.

Imidazole Derivatives.

Non-limiting examples of imidazole derivatives include clonidine, lofexidine, phentolamine, tiamenidine and tolonidine.

Quanternary Ammonium Compounds.

Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives.

Non-limiting examples of reserpine derivatives include bietaserpine, deserpidine, rescinnamine, reserpine and syrosingopine.

Suflonamide Derivatives.

Non-limiting examples of sulfonamide derivatives include ambuside, clopamide, furosemide, indapamide, quinethazone, tripamide and xipamide.

(7) Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

g. Treatment Agents for Congestive Heart Failure

Non-limiting examples of agents for the treatment of congestive heart failure include anti-angiotension II agents, afterload-preload reduction treatment, diuretics and inotropic agents.

(1) Afterload-Preload Reduction

In certain embodiments, an animal patient that can not tolerate an angiotension antagonist may be treated with a combination therapy. Such therapy may combine administration of hydralazine (apresoline) and isosorbide dinitrate (isordil, sorbitrate).

(2) Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea.

(3) Inotropic Agents

Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include enoximone and aminone (inocor).

(4) Antianginal Agents

Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

2. Surgical Therapeutic Agents

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

IV. KITS

In some embodiments, the present invention provides kits for the detection of PDE3A polymorphisms. In some embodiments, the kits contain reagents specific for the detection or analysis of DNA (e.g., oligonucleotide probes or primers). In preferred embodiments, the kits contain all of the components necessary to perform a detection assay, including all controls, directions for performing assays, and any necessary software for analysis and presentation of results. In some embodiments, individual probes and reagents for detection of PDE3A polymorphisms are provided as analyte specific reagents. In other embodiments, the kits are provided as in vitro diagnostics.

V. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

A Polymorphism in the PDE3A Gene Promoter that Prevents cAMP-Induced Increases in Transcriptional Activity, and Protects Against PDE3A Inhibitor Drug Tolerance The phosphodiesterase (PDE3A) 3A protein gene product regulates contractile function, via its co-localization in the cardiac myocyte phospholamban-Serca2a microdomain. Drugs that inhibit PDE3A (PDEIs) are positive inotropic and lusitropic agents, but exhibit therapeutic response heterogeneity that may be explained by varying degrees of PDEI tolerance. This led the inventors to search for functionally important genetic variation in the PDE3A gene (FIG. 1).

Figure 2:
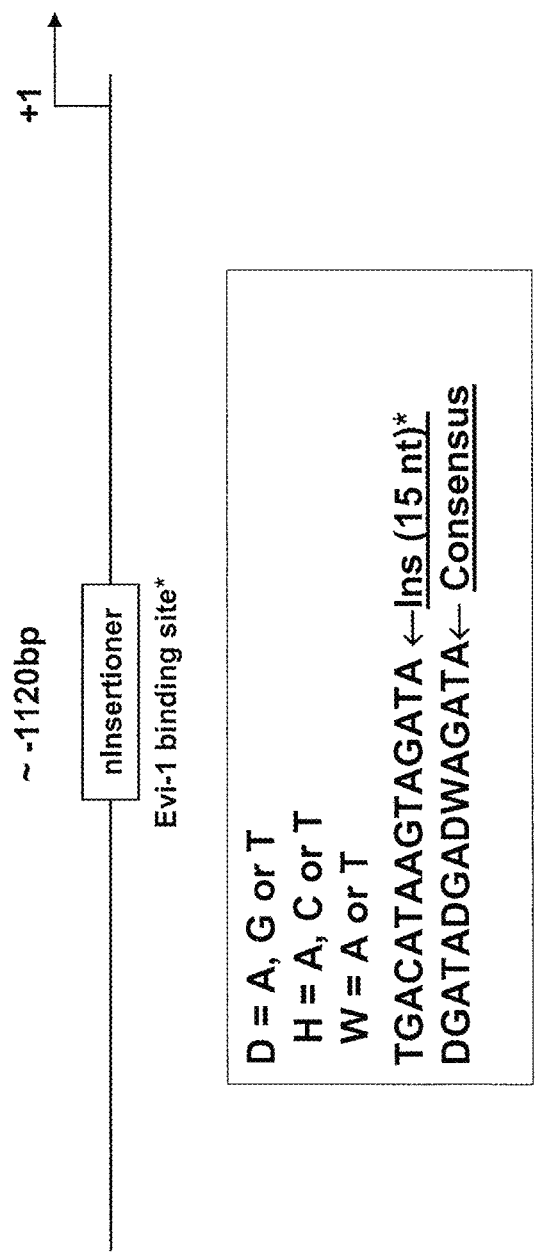
FIG. 2. Ins/Del Polymorphism in the PDE3A promoter region. Twenty-nine nucleotide insertion/deletion within the 2 kb proximal promoter region. This region contains the binding site for the Evi-1 (ectotropic viral integration site-1) transcription factor, a strong repressor. Evi-1 is an inhibitory factor and its expression is increased in response to cAMP. Genotype frequencies: deletion homozygotes: 37%; heterozygotes: 44%; insertion homozygotes: 19%. Allele frequencies: —Del: 59%; —Ins: 41%.
Figure 3:
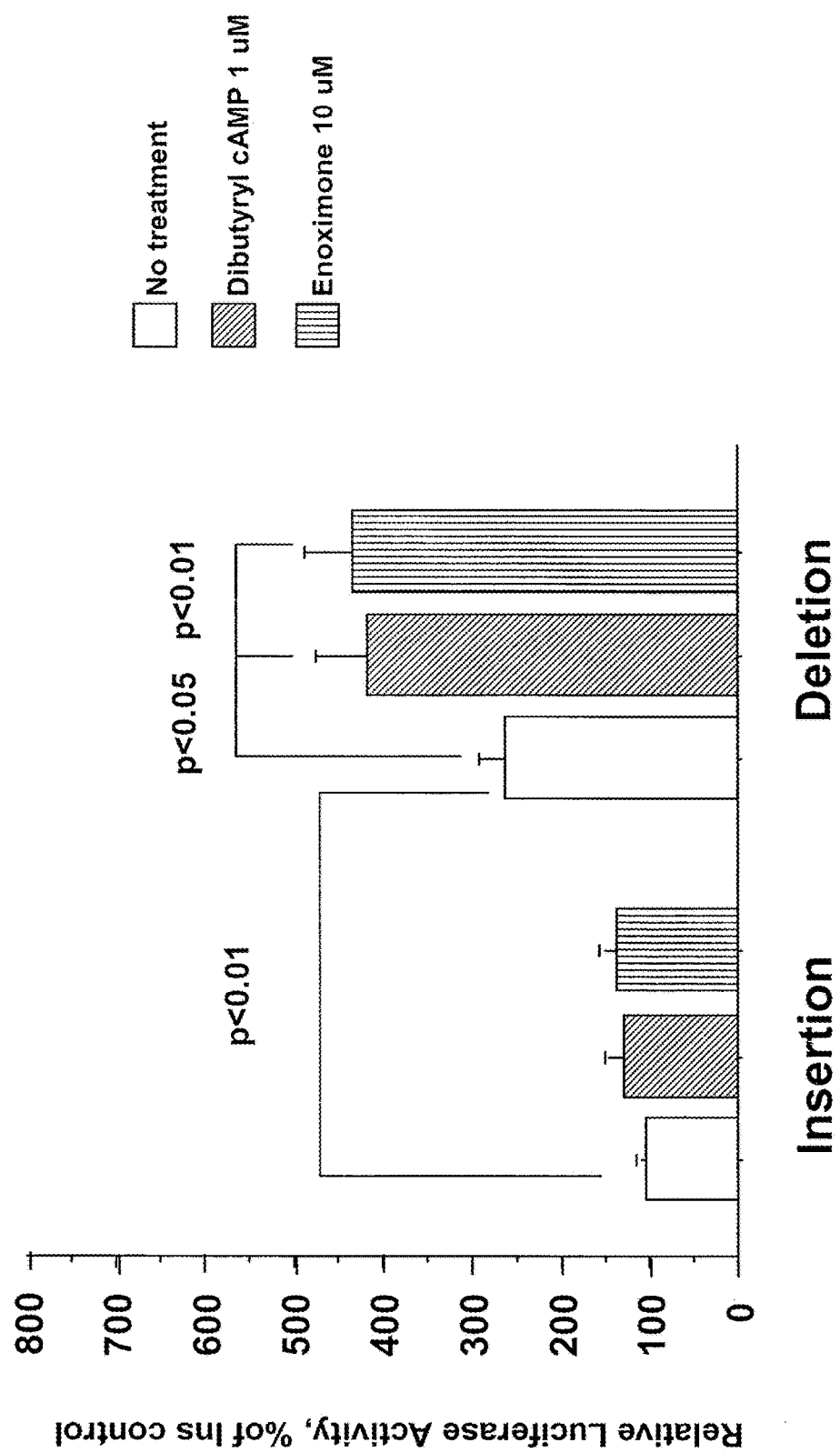
FIG. 3. NRVMs transfected with PDE3A Del/Ins luciferase constructs: agents that ↑ cAMP increase promoter activity in Del, not in Ins.
Figure 4:
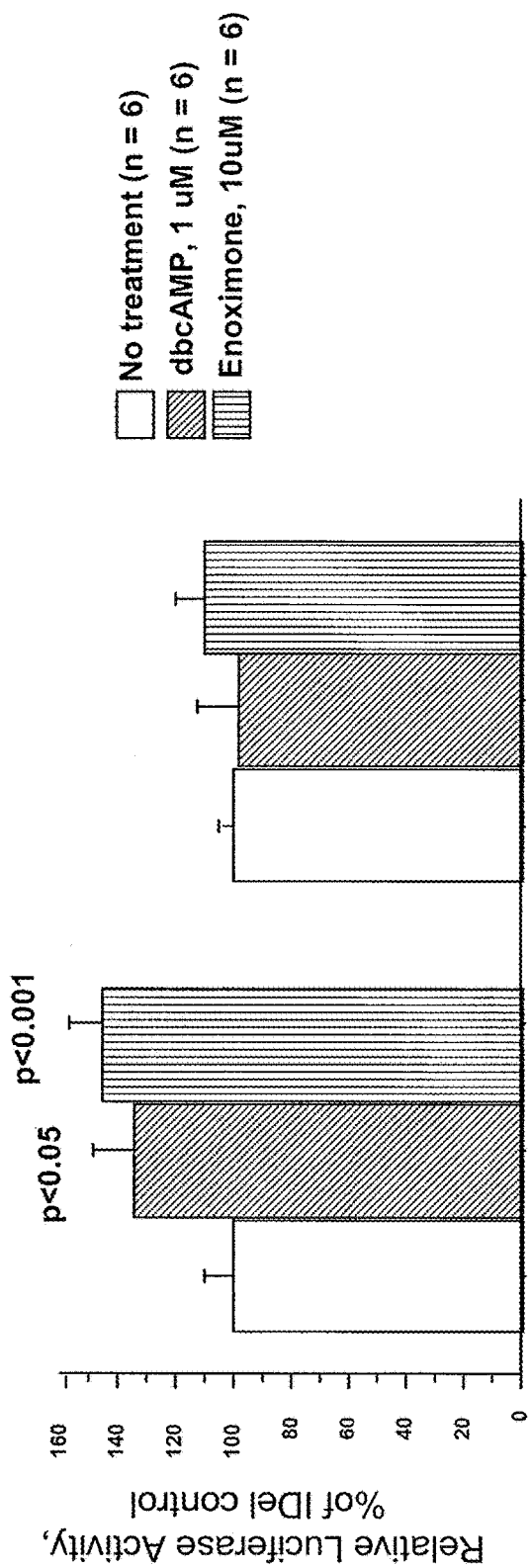
FIG. 4. Deletion of the CREB binding site (CRE) at −1070 abolishes promoter response to enoximone and dbcAMP in NRVMs transfected with the Del construct. Note: ~20 C/EBP binding sites distributed throughout entire promoter region.
Figure 4:
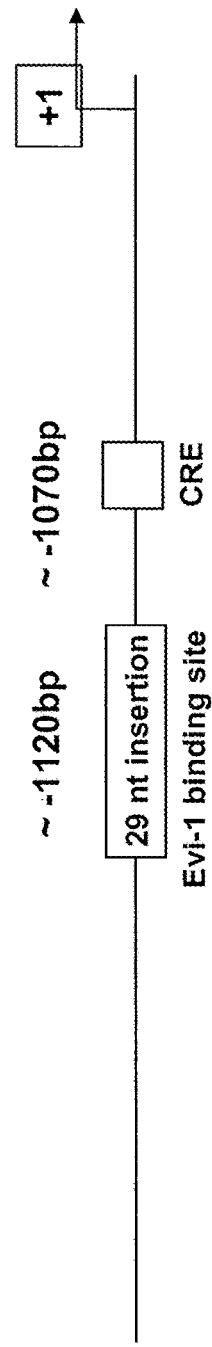
Figure 5:
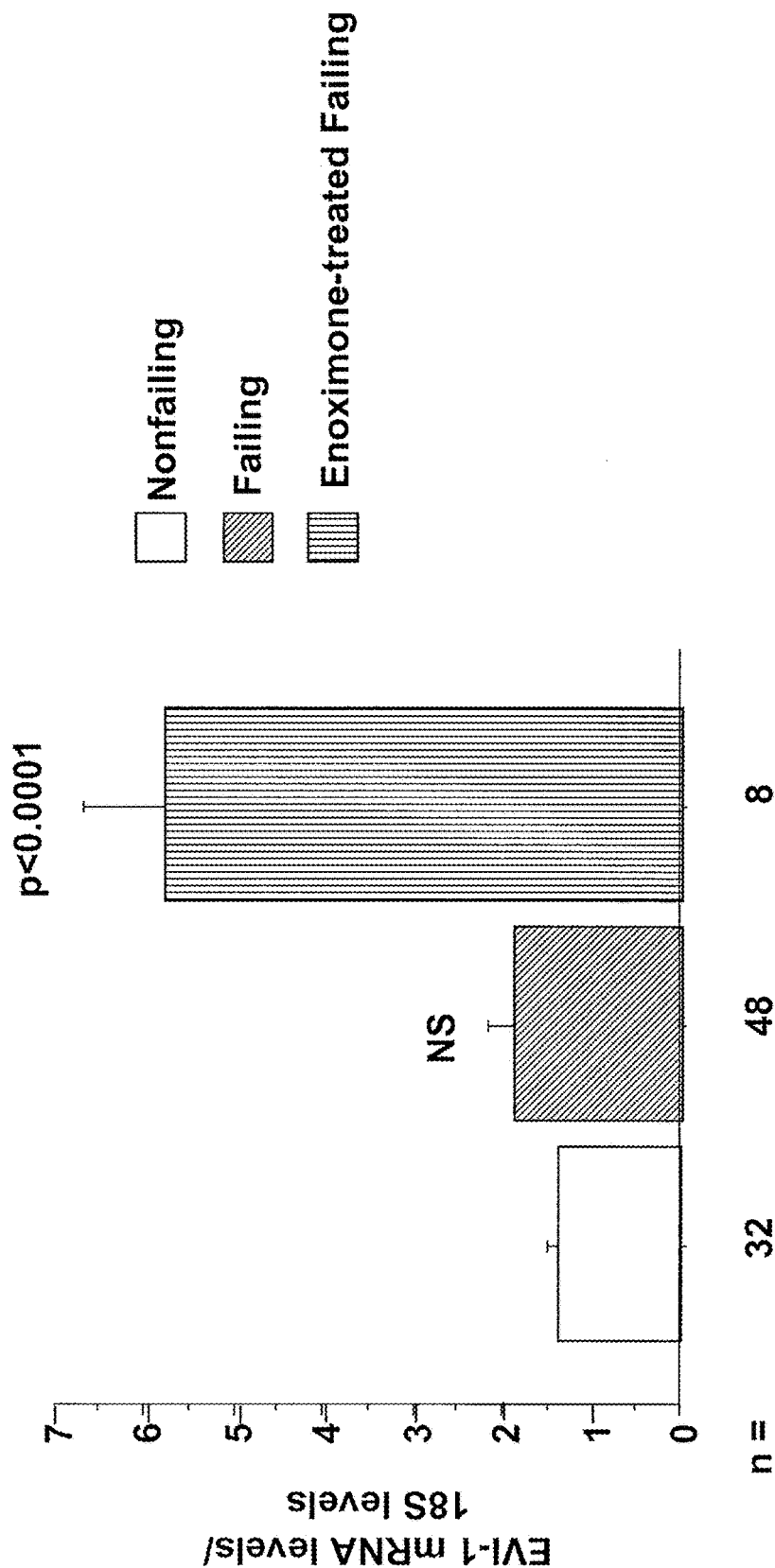
FIG. 5. In explanted LV samples from HF patients treated with enoximone, mRNA expression of the Evi-1 transcription factor is increased (p values compared to non-failing, no enoximone).
Figure 6:
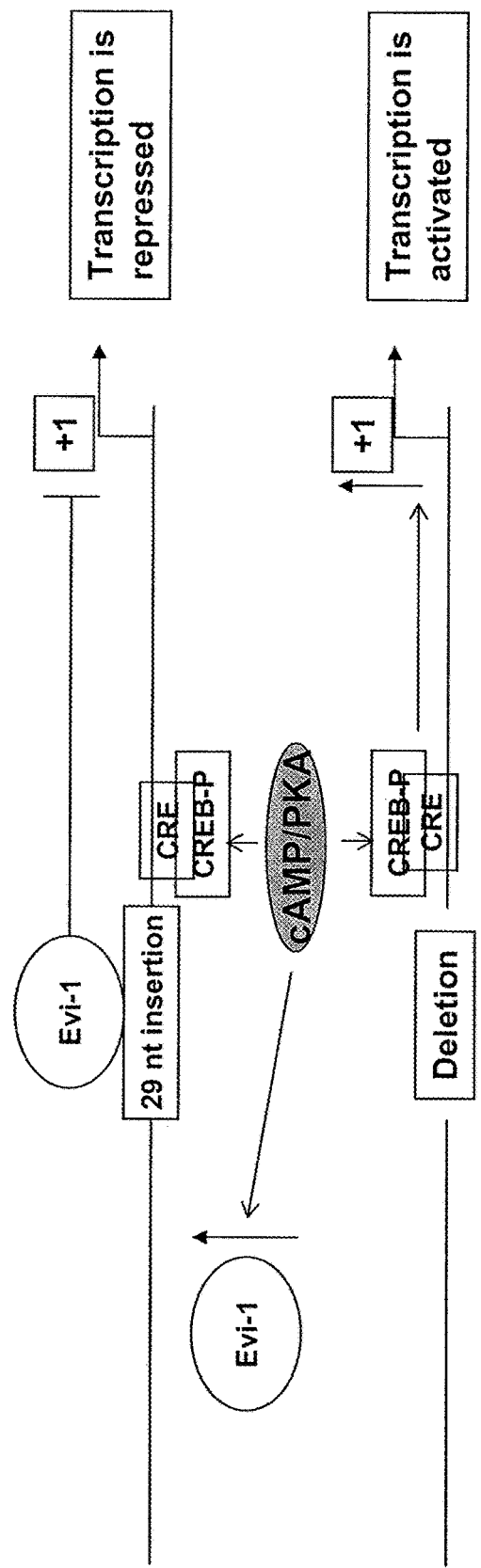
FIG. 6. Predicted model of INS/DEL polymorphism effects on PDE3A expression.
Figure 7:
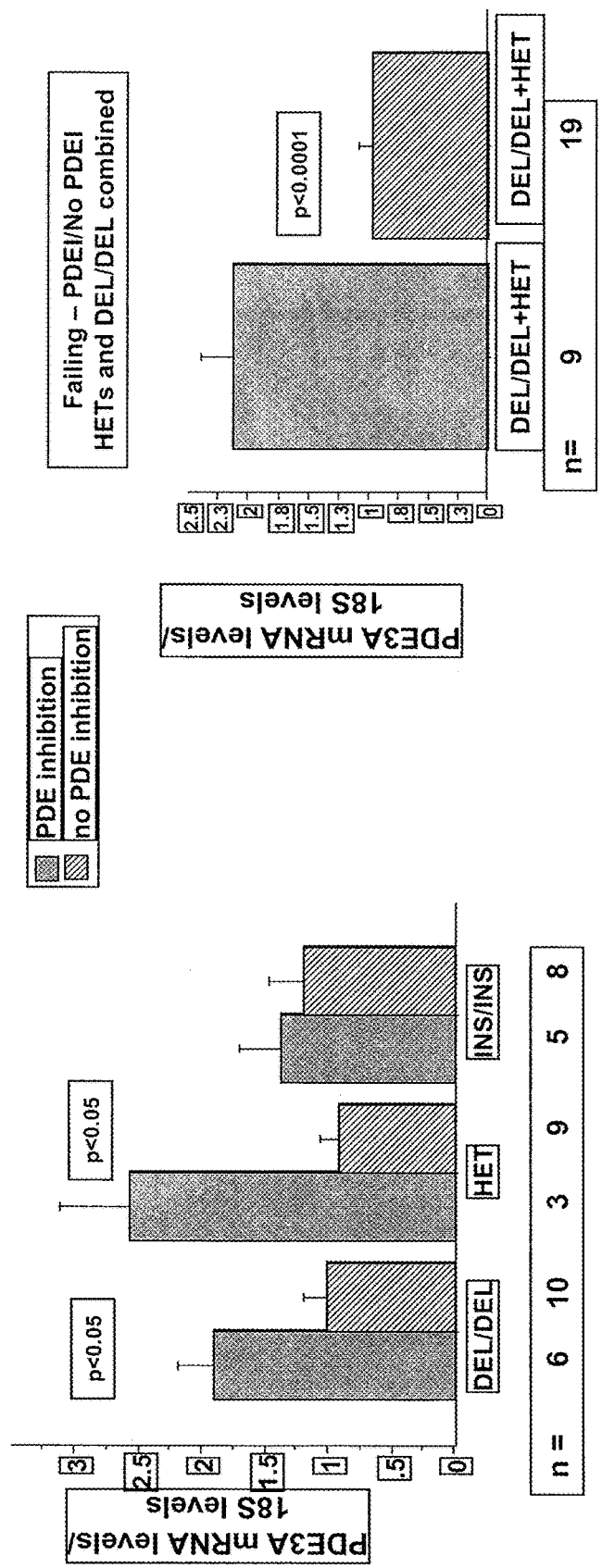
FIG. 7. PDE inhibition results in increased PDE3A mRNA expression in failing human hearts that are not homozygous for the INS polymorphism (Del carriers). Hypothesis: patients who are INS/INS will not develop tolerance to PDEIs. In DEL carriers CRE mediated feedback loop up-regulation in PDE3A gene expression by ↑ cAMP cancels effects of PDEIs.
Figure 8:
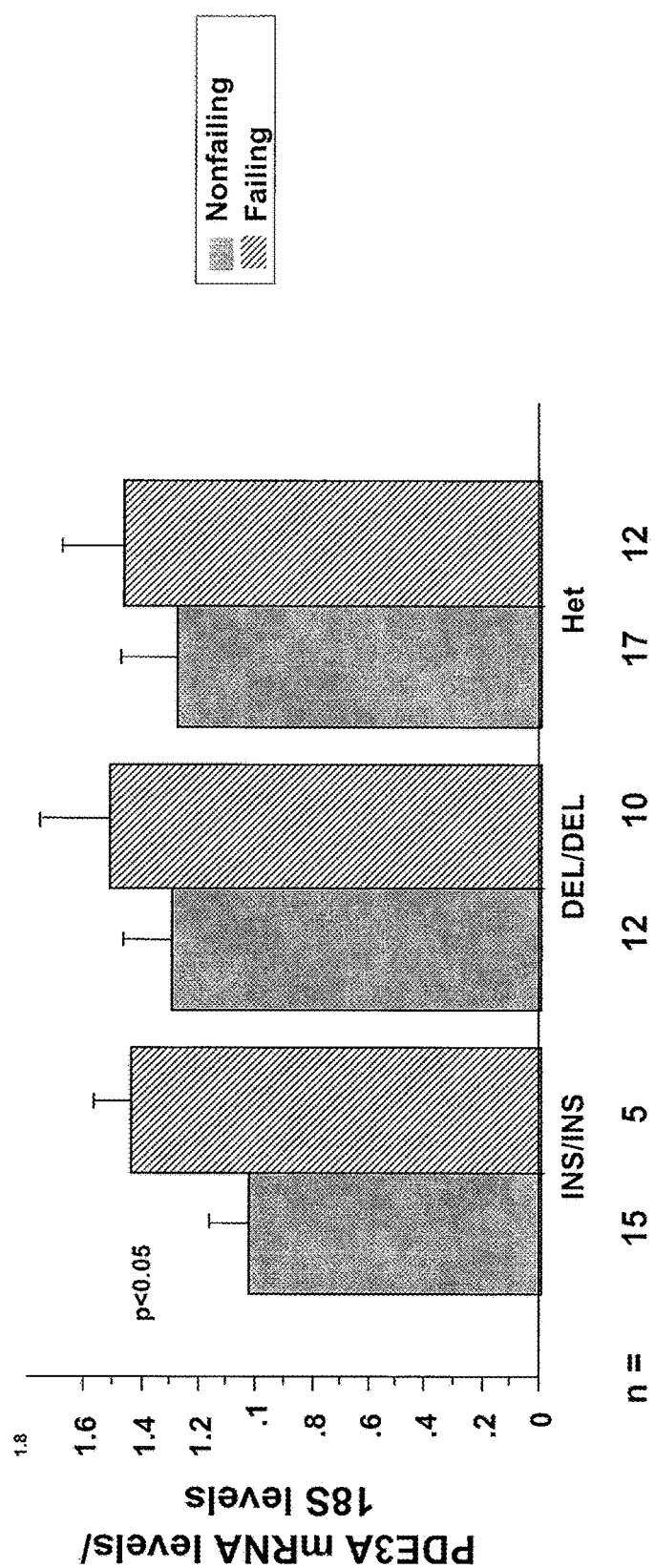
FIG. 8. PDE3A mRNA levels are up-regulated in the failing heart in patients that have the insertion polymorphism. Myocardial cAMP levels are decreased in HF, which is consistent with increased mRNA levels in INS/INS hearts. Evi-1 binds to the INS and down-regulates expression of PDE3A. Failing hearts have lower cAMP levels, and therefore there is less repression of PDE3A gene expression compared to nonfailing controls in individuals who are INS/INS.

The inventors identified a 29 nt insertion/deletion (Ins/Del, allele frequencies 0.41/0.59) polymorphism in the PDE3A promoter region, at −1120 from one of the start sites (FIG. 2). The Ins contains a binding site for ectotropic viral integration site-1 (Evi-1), a transcription factor that is markedly induced (by 16-fold) by cAMP. Evi-1 typically functions as a strong transcriptional repressor. In explanted left ventricular samples (LVs) from heart failure (HF) patients treated with enoximone, mRNA expression of Evi-1 is increased (FIG. 5). In LVs explanted from end-stage HF patients undergoing transplantation, patients treated with enoximone who were either homozygous or heterozygous for PDE3A Del (Del carriers, n=9), PDE3A mRNA abundance was increased 2.1±0.3 fold compared to Del patients not receiving enoximone (n=19, p<0.001) (FIG. 7). In contrast, LV samples from patients treated with enoximone who were homozygous for the Ins (Ins/Ins) did not exhibit an increase in PDE3A gene expression (1.1±0.3 fold, p=0.7) (FIG. 7). In neonatal rat cardiac myocytes (NRVMs) transfected with either Ins or Del PDE3A promoter-luciferase constructs, agents that increased cAMP markedly increased transcriptional activity in Del but not Ins (FIG. 3). However, deletion of the CREB binding site (CRE) at −1070 abolishes the promoter response to enoximone and dbcAMP in NRVMs transfected with the Del construct (FIG. 4). PDE3A mRNA levels are upregulated in failing heart patients with the Ins polymorphism (FIG. 8).

A 29 nt Ins/Del polymorphism in the PDE3A promoter regulates PDE3A gene expression, whereby the major allele, Del variant exhibits increased PDE3A expression in response to agents that increase cAMP. This provided a molecular explanation of tolerance to PDE3 inhibitors. In contrast, patients who are Ins/Ins exhibit no such up-regulation of PDE3A gene expression in response to cAMP augmenting agents, and as a result may not be predisposed to drug tolerance.

Example 2

Clinical Use of Enoximone

Patients.

Inclusion criteria can include: age >18 years; heart failure (HF) caused by ischemic or nonischemic cardiomyopathy; LV systolic dysfunction shown by an ejection fraction (EF)≤30%, detected on radionuclide ventriculography, two-dimensional echocardiography, or nuclear magnetic resonance imaging; an echocardiographically determined LV end-diastolic diameter >3.2 cm/m$^2$ or ≥6.0 cm; symptoms of dyspnoea or fatigue at rest or at minimal exertion [New York Heart Association (NYHA) class III-IV] for >2 months; at least one hospitalization or two outpatient visits requiring intravenous diuretic or vasodilator therapy within 12 months before screening; and optimal medical therapy including diuretics, beta-blockers, and angiotensin-converting enzyme (ACE)-inhibitors or angiotensin receptor blockers (ARBs) unless intolerant or contraindicated.

Dosing.

Drug dose can be 25-100 mg three times daily. Patients are re-evaluated at 1 and 2 weeks. Drug dose can be up-titrated to 50 mg or more three times daily in patients weighing more than 50 kg without renal and hepatic dysfunction. Patients will undergo follow-up clinical visits at 1, 2, 4, 6, 8, 9, 12 months and, in the following years, every 4 months. Each visit includes clinical examination and blood sampling for analysis of serum bilirubin, creatinine, and potassium.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference.

U.S. Pat. No. 4,582,788
U.S. Pat. No. 4,627,429
U.S. Pat. No. 4,659,774
U.S. Pat. No. 4,683,194
U.S. Pat. No. 4,683,195
U.S. Pat. No. 4,683,202
U.S. Pat. No. 4,784,857
U.S. Pat. No. 4,800,159
U.S. Pat. No. 4,816,571
U.S. Pat. No. 4,883,750
U.S. Pat. No. 4,946,773
U.S. Pat. No. 4,959,463
U.S. Pat. No. 4,965,188
U.S. Pat. No. 5,126,145
U.S. Pat. No. 5,130,238
U.S. Pat. No. 5,141,813
U.S. Pat. No. 5,169,766
U.S. Pat. No. 5,264,566
U.S. Pat. No. 5,279,721
U.S. Pat. No. 5,428,148
U.S. Pat. No. 5,554,744
U.S. Pat. No. 5,574,146
U.S. Pat. No. 5,602,244
U.S. Pat. No. 5,605,798
U.S. Pat. No. 5,645,897
U.S. Pat. No. 5,662,925
U.S. Pat. No. 5,705,629
U.S. Pat. No. 5,788,983
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,483
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,770
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,337
U.S. Pat. No. 5,866,366
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630

U.S. Pat. No. 5,922,574
U.S. Pat. No. 5,925,517
U.S. Pat. No. 5,925,525
U.S. Pat. No. 5,928,862
U.S. Pat. No. 5,928,869
U.S. Pat. No. 5,928,870
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 5,952,174
U.S. Pat. No. 6,113,940
U.S. Pat. No. 4,656,127
U.S. Pat. No. 4,682,195
Ausubel et al., Current Protocols in Molecular Biology, John Wiley & Sons, NY, 1989.
Barany, et al., Proc. Natl. Acad. Sci. USA, 88:189-193, 1991.
Bellus, J. Macromol. Sci. Pure Appl. Chem., A31(1): 1355-1376, 1994.
de Arruda et al., Expert. Rev. Mol. Diagn., 2:487-496, 2002.
Ding et al., Circulation, 111:2469-2476, 2005.
Durand et al., Ann. Med., 27:311-317, 1995.
European Appln. 201,184
European Appln. 237,362
European Appln. 258,017
European Appln. 266,032
European Appln. 320 308
European Appln. 329,822
European Appln. 50,424
European Appln. 84,796
French Patent 2,650,840
Froehler et al., Nucleic Acids Res., 14(13):5399-5407, 1986.
Frohman, In: PCR Protocols: A Guide To Methods And Applications, Academic Press, N.Y., 1990.
Great Britain Appln. 2 202 328
Halushka et al., Nat. Genet., 22(3):239-247, 1999.
Humphries, et al., In: Molecular Diagnosis of Genetic Diseases, Elles (Ed.), 321-340, 1996.
Inazuka et al., Genome Res, 7(11):1094-1103, 1997.
Innis et al., Proc. Natl. Acad. Sci. USA, 85(24):9436-9440, 1988.
Johnson et al., Nat. Genet., 29(2):233-237, 2001.
Jones, Nature, 199:280-282, 1963.
Ke and Cardon Bioinformatics, 19(2):287-288, 2003.
Klaassen's The Pharmacological Basis of Therapeutics
Komher, et al., Nucl. Acids. Res. 17:7779-7784, 1989.
Kuppuswamy et al., Proc. Natl. Acad. Sci. USA, 88:1143-1147, 1991.
Kwoh et al., Proc. Natl. Acad. Sci. USA, 86:1173, 1989.
Kwok and Chen, Curr Issues Mol. Biol., 5(2):43-60, 2003.
Kwok et al., Genomics, 23(1):138-144, 1994.
Kwok et al., Genomics, 31(1):123-6, 1996.
Kwok, Annu. Rev. Genomics Hum. Genet., 2:235-258, 2001.
Landegren et al., Science 241:1077-1080, 1988.
Lu et al., Biopolymers, 73:606-613, 2004.
Maxam et al., Proc. Natl. Acad. Sci. USA, 74:560, 1977.
Meyers et al., Science, 230:1242, 1985.
Modrich, Ann. Rev. Genet., 25:229-253, 1991.
Movsesian, J. Am. Coll. Cardiol., 34:318-324, 1999.
Mullis et al., Cold Spring Harbor Symp. Quant. Biol. 51:263-273, 1986.
Nickerson et al., Proc. Natl. Acad. Sci. USA, 87:8923-8927, 1990.
Nyren et al., Anal. Biochem. 208:171-175, 1993.
Ohara et al., Proc. Natl. Acad. Sci. USA, 86:5673-5677, 1989.
Orita et al., Genomics, 5:874-879, 1989.
PCT Appln. PCT/US87/00880
PCT Appln. PCT/US89/01025
PCT Appln. WO 88/10315
PCT Appln. WO 89/06700
PCT Appln. WO 93/22456
PCT Appln. WO 95/11995
PCT Appln. WO 89/06700
PCT Appln. WO 90/01069
PCT Appln. WO 91/02087
PCT Appln. WO 92/15712
Physicians Desk Reference
Prezant et al., Hum. Mutat., 1:159-164, 1992.
Reinhardt et al., J. Clin. Invest., 95:1528-1538, 1995.
Remington's Pharmaceutical Sciences, 15th Edition, pages 1035-1038 and 1570-1580. 1990.
Ruano et al., Nucl. Acids Res., 19:6877-6882, 1991.
Ruano et al., Nucl. Acids Res., 17:8392, 1989.
Sambrook et al., In: Molecular cloning, Cold Spring Harbor Laboratory Press, Cold Spring Harbor, N.Y., 2001.
Sanger et al., J. Molec. Biol., 94:441, 1975.
Shakur et al., Prog. Nucleic Acids Res. Mol. Biol., 66:241-277, 2000.
Sheffield et al., Proc. Natl. Acad. Sci. USA, 86:232-236, 1989.
Small et al., Methods Enzymol, 343:459-75, 2002.
Sokolov, Nucl. Acids Res. 18:3671, 1990.
Stevens et al., Biotechniques, 34:198-203, 2003.
Syvanen et al., Genomics 8:684-692, 1990.
Taillon-Miller et al., Genome Res, 8(7):748-754, 1998.
The Merck Index, Eleventh Edition
Turki et al., J. Clin. Invest., 95:1635-1641, 1995.
Ugozzoll et al., GATA 9:107-112, 1992.
Walker et al., Proc. Natl. Acad. Sci. USA, 89:392-396, 1992.
Wang and Dhalla, Mol. Cell Biochem., 214:131-155, 2000.
Wartell et al., Nucl. Acids Res., 18:2699-2706, 1990.
Winter et al., Proc. Natl. Acad. Sci. USA, 82:7575, 1985.

The invention claimed is:

1. A method for treating a human patient with heart failure comprising treating the patient with an effective amount of a PDE3A inhibitor after the patient is determined to be homozygous for an insertion of an ectotropic viral integration site-1 (Evi-1) binding site in the phosphodiesterase type 3A (PDE3A) gene promoter, wherein the Evi-1 binding site insertion is 85% identical to SEQ ID NO:2 and is located within 2000 nucleotides 5' of the PDE3A gene transcriptional initiation site and wherein the PDE3A inhibitor is amrinone, cilostazol, milrinone, quazinone, siguazodan, trequinsin, or enoximone.

2. The method of claim 1, wherein the PDE3A inhibitor is enoximone.

3. The method of claim 1, wherein the PDE3A inhibitor is administered at the dose of 15 mg to 100 mg.

4. The method of claim 1, wherein the PDE3A inhibitor is administered 1, 2, 3 or more times a day.

5. The method of claim 1, wherein the PDE3A inhibitor is administered 1, 2, 3, 4, 5 or more times a week.

6. The method of claim 1, wherein the insertion is 29 nucleotides in length.

7. The method of claim 1, wherein the insertion is identical to SEQ ID NO:2.

8. A method for treating a patient with heart failure comprising treating the patient with an effective amount of a enoximone after the patient is determined to be homozygous for an insertion having a sequence identical to SEQ ID NO:2 and located within 2000 nucleotides 5' of the PDE3A gene transcriptional initiation site.

9. The method of claim 8, wherein the patient is determined to be homozygous for an Evi-1 insertion based on analyzing a sample of the patient by performing nucleic acid sequencing, restriction digestion, allele-specific nucleic acid amplification, single-stranded conformational polymorphism analysis, or allele specific hybridization analysis.

10. The method of claim 8, wherein enoximone is administered at the dose of 15 mg to 100 mg.

11. The method of claim 8, wherein enoximone is administered 1, 2, 3 or more times a day.

12. The method of claim 8, wherein enoximone is administered 1, 2, 3, 4, 5 or more times a week.

* * * * *